US012629381B2

(12) United States Patent
Kadajji et al.

(10) Patent No.: US 12,629,381 B2
(45) Date of Patent: May 19, 2026

(54) PROLIPOSOMAL TESTOSTERONE UNDECANOATE FORMULATIONS

(71) Applicant: TESORX PHARMA, LLC, Menlo Park, CA (US)

(72) Inventors: Veeran Gowda Kadajji, North Hollywood, CA (US); Natarajan Venkatesan, Diamond Bar, CA (US); Nitin K. Swarnakar, Suffern, NY (US); Teresa Hong, El Monte, CA (US); Ramachandran Thirucote, Atherton, CA (US); Guru V. Betageri, Chino Hills, CA (US)

( * ) Notice: Subject to any disclaimer, the term of this patent is extended or adjusted under 35 U.S.C. 154(b) by 1109 days.

(21) Appl. No.: 17/631,525

(22) PCT Filed: Aug. 10, 2020

(86) PCT No.: PCT/US2020/045607
§ 371 (c)(1),
(2) Date: Jan. 31, 2022

(87) PCT Pub. No.: WO2021/030260
PCT Pub. Date: Feb. 18, 2021

(65) Prior Publication Data
US 2022/0265679 A1 Aug. 25, 2022

Related U.S. Application Data

(60) Provisional application No. 62/884,919, filed on Aug. 9, 2019.

(51) Int. Cl.
*A61K 31/568* (2006.01)
*A61K 9/127* (2006.01)
*A61K 9/48* (2006.01)

(52) U.S. Cl.
CPC ............ *A61K 31/568* (2013.01); *A61K 9/127* (2013.01); *A61K 9/4891* (2013.01)

(58) Field of Classification Search
CPC .... A61K 31/568; A61K 9/127; A61K 9/4891; A61K 9/0053; A61K 9/1277; A61K 9/145; A61K 9/0095; A61K 47/24; A61K 47/26; A61P 1/16; A61P 5/06; A61P 5/24; A61P 5/26; A61P 13/12; A61P 15/08
See application file for complete search history.

(56) References Cited

U.S. PATENT DOCUMENTS

| 9,844,557 B2 * | 12/2017 | Betageri ................. A61P 21/00 |
| 2002/0187189 A1 | 12/2002 | Betageri |
| 2014/0112986 A1 | 4/2014 | Betageri et al. |

FOREIGN PATENT DOCUMENTS

| WO | 2014160392 A1 | 10/2014 |
| WO | 2017/120592 A1 | 7/2017 |
| WO | WO-2018089759 A1 * | 5/2018 ........... A61K 31/337 |

OTHER PUBLICATIONS

International Search Report and Written Opinion in International Application No. PCT/US2020/045607, dated Nov. 18, 2020.

* cited by examiner

Primary Examiner — Robert A Wax
Assistant Examiner — Ngoc-Anh Thi Nguyen
(74) Attorney, Agent, or Firm — RAPHAEL BELLUM PLLC

(57) ABSTRACT

This invention relates to proliposomal powder dispersions of testosterone undecanoate (TU) and phospholipids, including dispersions of TU and palmitoylphosphatidylcholine (DPPC), wherein the weight/weight (w/w) ratio of TU:DPPC in the proliposomal powder dispersion is about 1:2; or TU and 1,2-dimyristoyl-sn-glycero-3-phosphocholine (DMPC), wherein the weight/weight (w/w) ratio of TU:DMPC in the proliposomal powder dispersion is about 1:3; or TU and a 1-myristoyl-2-palmitoyl-sn-glycero 3-phosphocholine (MPPC), wherein the weight/weight (w/w) ratio of TU:MPPC in the proliposomal powder dispersion is about 1:3.

12 Claims, 29 Drawing Sheets

Plasma Testosterone Undecanoate Levels in Female Dogs
Following Single Dose PO Administration of TSX-011 (31.6 mg)

Average Plasma Testosterone Undecanoate Levels in Female Dogs
Following Single Dose PO Administration of TSX-011 (31.6 mg)

Average Plasma Testosterone Levels in Female Dogs Following Single
Dose PO Administration of TSX Formulations (n=6±sd)

Average Plasma Testosterone Levels in Female Dogs
Following Single Dose PO Administration of TSX Formulations
(n=5±sd) - Dose Normalized to TSX-011

Predose baseline

End of study

30 mg bid D1

30 mg bid D5

PROLIPOSOMAL TESTOSTERONE UNDECANOATE FORMULATIONS

CROSS-REFERENCE TO RELATED APPLICATIONS

This application claims priority to U.S. Application No. 62/884,919, filed 9 Aug. 2019, which is incorporated here in its entirety.

FIELD OF THE INVENTION

The invention relates to proliposomal powder dispersions of testosterone undecanoate and phospholipids, and improved bioavailability of orally-administered testosterone undeconoate.

BACKGROUND

A goal of testosterone replacement therapy (TRT) is to restore low endogenous plasma levels of testosterone to a normal physiological levels. Restoration of normal physiological levels in patients can alleviate symptoms suggestive of hormone deficiency, or for some individuals, result in a more masculine appearance and identity. A convenient form of TRT relies on oral administration of testosterone undecanoate (TU). However, the performance of currently marketed oral dosage forms for TU varies significantly, depending on when an individual ingests the dosage form, relative to meal times. See Yin et al. The following description, however, shows that TU can be combined with certain phospholipids in specified ratios to form a proliposomal powder disperstion that can be incorporated into a dry, free-flowing powder that will form readily absorbable liposome-encapsulated TU. Moreover, because proliposomal formulation are dry powders, they, unlike liquid suspensions of liposomes, can be incorporated into oral dosage forms with an enteric coating to protect the formulation until it reaches the less hostile, aqueous environment of the small intestine, where hydration of the prolipomal powder dispersion can occur to cause the formation of liposomes that deliver TU to the intestinal epithelium.

SUMMARY OF THE INVENTION

This invention relates to proliposomal powder dispersions of testosterone undecanoate (TU) and a phospholipid. For example, a proliposomal powder dispersion of the invention may contain TU in a dispersion with:

(A) dipalmitoylphosphatidylcholine (DPPC), wherein the weight/weight (w/w) ratio of TU:DPPC in the proliposomal powder dispersion is about 1:2; or (B) 1,2-dimyristoyl-sn-glycero-3-phosphocholine (DMPC), wherein the weight/weight (w/w) ratio of TU:DMPC in the proliposomal powder dispersion is about 1:3; or (C) 1-myristoyl-2-palmitoyl-sn-glycero 3-phosphocholine (MPPC), wherein the weight/weight (w/w) ratio of TU:MPPC in the proliposomal powder dispersion is about 1:3.

Proliposomal powder dispersions of the invention may also be included in dosage forms suitable for oral administration. In that regard, some oral dosage forms of the invention further include mannitol. Accordingly, an oral dosage form of the invention may, for example, contain:

(A) a proliposomal powder dispersion of TU and DPPC in a w/w ratio of about 1:2, combined with mannitol, such that the w/w ratio of the proliposomal powder dispersion to mannitol is about 1:1.25; or (B) a proliposomal powder dispersion of TU and DMPC in a w/w ratio of about 1:3, combined with mannitol, such that the w/w ratio of the proliposomal powder dispersion to mannitol is about 1:1.25; or (C) a proliposomal powder dispersion of TU and MPPC in a w/w ratio of about 1:3, combined with mannitol, such that the w/w ratio of the proliposomal powder dispersion to mannitol is about 1:1.25.

Furthermore, as dosage forms of the invention may be suited for oral administration, in some embodiments, an oral dosage form of the invention may be in a capsule or tablet form, optionally, an enteric-coated capsule.

Proliposomal powder dispersions and oral dosage forms of the invention may be used in methods for treating individuals for conditions and disorders associated with, or caused by low blood plasma levels of endogenous testosterone. Accordingly, a proliposomal powder dispersion or oral dosage form of the invention may be used in a method of testosterone replacement therapy (TRT) for an individual in need thereof. A method of TRT may, for example, treat a condition in which a low endogenous level of testosterone results from an injury, an infection, a loss of the testicles, chemotherapy, radiation treatment, genetic abnormalities, hemochromatosis, dysfunction of the pituitary gland, inflammatory disease, medication side effect, chronic kidney failure, liver cirrhosis, stress, alcoholism, obesity, Kallman's syndrome, male hypogonadism, testosterone deficiency syndrome (TDS), or any disorder or condition in which pre-therapy plasma level of testosterone is 300 ng/dL or less.

DETAILED DESCRIPTION

Figure 1:
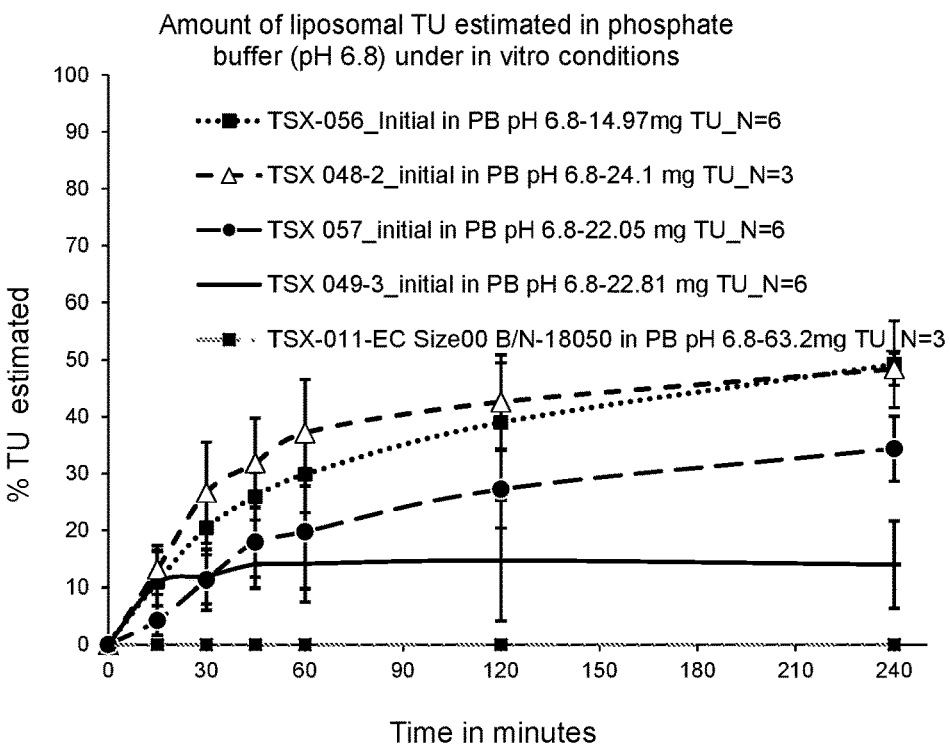
FIG. 1 shows the % amount of TU released from the following capsules containing TU proliposomal powder dispersion formulations over time in phosphate buffer (pH 6.8): TSX-011 (TU:DSPC=1:2); TSX-048 (TU:DMPC=1:3); TSX:049 (TU:DPPC=1:2); TSX-056 (TU:MPPC=1:3); and TSX-057 (TU:(DPPC+Oleic Acid)=1:2). n=3/capsule formulation for TSX-011 and TSX-048. n=6/capsule formulation for TSX-049, TSX-056, and TSX-057.

The following description discloses the invention according to embodiments related to proliposomal powder dispersions of testosterone undecanoate (TU) and a phospholipid, as well as dosage forms containing such dispersions, and methods of treating conditions and disorders associated with, or caused by low blood plasma levels of endogenous testosterone. A "proliposomal powder dispersion" of TU and a phospholipid is a mixture in which the TU and phospholipid are dispersed as one in another. Proliposomal powder dispersions of the invention form liposomes upon contact with water or an aqueous solution, including, for example, fluids of the gastrointestinal tract.

Testosterone undecanoate as described here, is the synthetic androstane steroid, testosterone 17β-undecanoate. The phospholipid component of a proliposomal powder dispersion of the invention preferrably refers to dipalmitoylphosphatidylcholine (DPPC), 1,2-dimyristoyl-sn-glycero-3-phosphocholine (DMPC), or 1-myristoyl-2-palmitoyl-sn-glycero 3-phosphocholine (MPPC). In some embodiments of the invention, the proliposomal powder dispersion contains TU in a dispersion with DPPC, in which the weight/weight (w/w) ratio of TU to DPPC, (i.e., TU:DPPC) is about 1:2. In other embodiments of the invention, the proliposomal powder dispersion contains TU in a dispersion with DMPC, in which the w/w ratio of TU to DMPC, (i.e., TU:DMPC) is about 1:3. Yet, in other embodiments of the invention, the proliposomal powder dispersion contains TU in a dispersion with MPPC, in which the w/w ratio of TU to MPPC, (i.e., TU:MPPC), is about 1:3. As used here, the term "about" provides flexibility to the w/w ratios of the proliposomal powder dispersions of the invention by indicating a particular ratio between components may be "a little less" or "a little more" than stated. For example, a "a little less" or "a little more" may indicate a variance of 10% or less. Accordingly, in some proliposomal powder dispersions of the invention, in which the w/w ratio of TU to DPPC is about 1:2, the ratio of TU:DPPC may be (0.9:2), (0.91:2), (0.92:2), (0.93:2), (0.94:2), (0.95:2), (0.96:2), (0.97:2), (0.98:2), (0.99:2), (1:2), (1.01:2), (1.02:2), (1.03:2), (1.04:2), (1.05: 2), (1.06:2), (1.07:2), (1.08:2), (1.09:2), (1.10:2), (1:1.99), (1:1.98), (1:1.97), (1:1.96), (1:1.95), (1:1.94), (1:1.93), (1:1.92), (1:1.91), (1:1.90), (1:1.89), (1:1.88), (1:1.87), (1:1.86), (1:1.85), (1:1.84), (1:1.83), (1:1.82), (1:1.81), (1:1.80), (1:2.01), (1:2.02), (1:2.03), (1:2.04), (1:2.05), (1:2.06), (1:2.07), (1:2.08), (1:2.09), (1:2.19), (1:2.2), or any ratio therein. Similarly, in other proliposomal powder dispersions of the invention, in which the w/w ratio of TU to DMPC is about 1:3, the ratio of TU:DMPC may be (0.9:3), (0.91:3), (0.92:3), (0.93:3), (0.94:3), (0.95:3), (0.96:3), (0.97:3), (0.98:3), (0.99:3), (1:3), (1.01:3), (1.02:3), (1.03: 3), (1.04:3), (1.05:3), (1.06:3), (1.07:3), (1.08:3), (1.09:3), (1.10:3), (1:2.99), (1:2.98), (1:2.97), (1:2.96), (1:2.95), (1:2.94), (1:2.93), (1:2.92), (1:2.91), (1:2.90), (1:2.89), (1:2.88), (1:2.87), (1:2.86), (1:2.85), (1:2.84), (1:2.83), (1:2.82), (1:2.81), (1:2.80), (1:2.79), (1:2.78), (1:2.77), (1:2.76), (1:2.75), (1:2.74), (1:2.73), (1:2.72), (1:2.71), (1:2.70), (1:3.01), (1:3.02), (1:3.03), (1:3.04), (1:3.05), (1:3.06), (1:3.07), (1:3.08), (1:3.09), (1:3.19), (1:3.2), (1:3.21), (1:3.22), (1:3.23), (1:3.24), (1:3.25), (1:3.26), (1:3.27), (1:3.28), (1:3.29), (1:3.3), or any ratio therein. In yet other proliposomal powder dispersions of the invention, in which the w/w ratio of TU to MPPC is about 1:3, the ratio of TU:MPPC may be (0.9:3), (0.91:3), (0.92:3), (0.93:3), (0.94:3), (0.95:3), (0.96:3), (0.97:3), (0.98:3), (0.99:3), (1:3), (1.01:3), (1.02:3), (1.03:3), (1.04:3), (1.05:3), (1.06: 3), (1.07:3), (1.08:3), (1.09:3), (1.10:3), (1:2.99), (1:2.98), (1:2.97), (1:2.96), (1:2.95), (1:2.94), (1:2.93), (1:2.92), (1:2.91), (1:2.90), (1:2.89), (1:2.88), (1:2.87), (1:2.86), (1:2.85), (1:2.84), (1:2.83), (1:2.82), (1:2.81), (1:2.80), (1:2.79), (1:2.78), (1:2.77), (1:2.76), (1:2.75), (1:2.74), (1:2.73), (1:2.72), (1:2.71), (1:2.70), (1:3.01), (1:3.02), (1:3.03), (1:3.04), (1:3.05), (1:3.06), (1:3.07), (1:3.08), (1:3.09), (1:3.19), (1:3.2), (1:3.21), (1:3.22), (1:3.23), (1:3.24), (1:3.25), (1:3.26), (1:3.27), (1:3.28), (1:3.29), (1:3.3), or any ratio therein.

A proliposomal powder dispersion of the invention can be prepared by methods known in the art, including the general methods for preparing proliposomal powder dispersions disclosed in PCT Patent Application Publication Nos. WO 2002/085304, WO 2013/170012, WO 2017/120586, and WO 2017/120592, which are all incorporated here in their entireities. Homogenizing steps can be performed at a high pressure and/or at a temperature higher than the Tc/Tg of the phospholipids. In some embodiments of the invention, the average particle size of a proliposomal powder dispersion can be reduced by grinding, passing the powder through screens, or by any other suitable technique. For example, the particles within a proliposomal powder dispersion may, but are not required to have a powder size ranging from about 10 to 200 mesh, 20 to 120 mesh or 40 to 60 or 60 to 80 mesh. In other embodiments of the invention, high-pressure homogenization can be used for the homgenization step to produce a proliposomal powder suspension with an average particle size (Zavg) of less than 200 nanometers (nm). Accordingly, some proliposomal powder dispersions of the invention have an average particle size of about 200 nm, 199 nm, 198 nm, 197 nm, 196 nm, 195 nm, 194 nm, 193 nm, 192 nm, 191 nm, 190 nm, 189 nm, 188 nm, 187 nm, 186 nm, 185 nm, 184 nm, 183 nm, 182 nm, 181 nm, 180 nm, 179 nm, 178 nm, 177 nm, 176 nm, 175 nm, 174 nm, 173 nm, 172 nm, 171 nm, 170 nm, or any size therein.

As stated above, the invention also relates to dosage forms, which contain proliposomal powder dispersions of the invention. More particularly, dosage forms of the invention are typically suitable for oral administration, and thus, may be called "oral dosage forms". In some embodiments of the invention, the proliposomal powder dispersion component of an oral dosage form, is mixed—typically admixed—with mannitol.

Accordingly, in one oral dosage form according to the invention, in which the proliposomal powder dispersion contains TU and DPPC in a w/w ratio of about 1:2, the proliposomal dispersion is in a mixture with mannitol, in which the w/w ratio of the proliposomal powder dispersion to mannitol is about 1:1.25. Therefore, consistent with the definition of "about", as described above with respect to TU and phospholipid components, the ratio of the proliposomal powder dispersion to mannitol in the foregoing oral dosage form may be (0.9:1.25), (0.91:1.25), (0.92:1.25), (0.93:1.25), (0.94:1.25), (0.95:1.25), (0.96:1.25), (0.97:1.25), (0.98:1.25), (0.99:1.25), (1:1.25), (1.01:1.25), (1.02:1.25), (1.03:1.25), (1.04:1.25), (1.05:1.25), (1.06:1.25), (1.07:1.25), (1.08:1.25), (1.09:1.25), (1.10:1.25), (1:1.24), (1:1.23), (1:1.22), (1:1.21), (1:1.20), (1:1.19), (1:1.18), (1:1.17), (1:1.16), (1:1.15), (1:1.14), (1:1.13), (1:1.26), (1:1.27), (1:1.28), (1:1.29), (1:1.30), (1:1.31), (1:1.32), (1:1.33), (1:1.34), (1:1.35), (1:1.36), (1:1.37), or any ratio therein.

In some other oral dosage form of the invention in which the proliposomal powder dispersion contains TU and DMPC in a w/w ratio of about 1:3 w/w ratio, the proliposomal powder dispersion is mixed with mannitol in a w/w ratio of about 1:1.25. Therefore, the ratio of the proliposomal powder dispersion to mannitol in the foregoing oral dosage form may be (0.9:1.25), (0.91:1.25), (0.92:1.25), (0.93:1.25), (0.94:1.25), (0.95:1.25), (0.96:1.25), (0.97:1.25), (0.98:1.25), (0.99:1.25), (1:1.25), (1.01:1.25), (1.02:1.25), (1.03:1.25), (1.04:1.25), (1.05:1.25), (1.06:1.25), (1.07:1.25), (1.08:1.25), (1.09:1.25), (1.10:1.25), (1:1.24), (1:1.23), (1:1.22), (1:1.21), (1:1.20), (1:1.19), (1:1.18), (1:1.17), (1:1.16), (1:1.15), (1:1.14), (1:1.13), (1:1.26), (1:1.27), (1:1.28), (1:1.29), (1:1.30), (1:1.31), (1:1.32), (1:1.33), (1:1.34), (1:1.35), (1:1.36), (1:1.37), or any ratio therein.

In yet another oral dosage form of the invention in which the proliposomal powder contains TU and MPPC in a w/w ratio of about 1:3 w/w ratio, the proliposomal powder dispersion is mixed with mannitol in a w/w ratio of about 1:1.25. Therefore, the ratio of the proliposomal powder dispersion to mannitol in the foregoing oral dosage form may be (0.9:1.25), (0.91:1.25), (0.92:1.25), (0.93:1.25), (0.94:1.25), (0.95:1.25), (0.96:1.25), (0.97:1.25), (0.98:1.25), (0.99:1.25), (1:1.25), (1.01:1.25), (1.02:1.25), (1.03:1.25), (1.04:1.25), (1.05:1.25), (1.06:1.25), (1.07:1.25), (1.08:1.25), (1.09:1.25), (1.10:1.25), (1:1.24), (1:1.23), (1:1.22), (1:1.21), (1:1.20), (1:1.19), (1:1.18), (1:1.17), (1:1.16), (1:1.15), (1:1.14), (1:1.13), (1:1.26), (1:1.27), (1:1.28), (1:1.29), (1:1.30), (1:1.31), (1:1.32), (1:1.33), (1:1.34), (1:1.35), (1:1.36), (1:1.37), or any ratio therein.

An oral dosage form of the invention can be a tablet or a capsule. Typically an oral dosage form according to the invention is a capsule. The capsules can be soft or hard capsules. More particularly, the capsule material of an oral dosage form of the invention is preferably, but not limited to, plant-derived hydroxypropyl methylcellulose (HPMC). For example, the capsule made from animal-derived gelatin or The size of a capsule for an oral dosage form of the invention can be any size that is sufficient to contain its proliposomal powder dispersion and excipient components. For example, the capsule can be a size 5, 4, 3, 2, 1, 0, 0E, 00, 000, 13, 12, 12el, 11, 10, 7, or Su07. Capsules are filled using any suitable techniques.

Filled capsules can be coated with an enteric coating. An enteric coating protects an oral dosage form of the invention from the harsh, acidic environment of the stomach, so that the release of the proliposomal powder dispersion can be delayed until the dosage form reaches the small intestine. Upon contact with small intestinal fluid, the proliposomal powder dispersion is hydrated, leading to the formation of liposomes and uptake of the TU through the small intestine epithelium or lymphatic system, or both. Any coatings of oral dosage forms of the invention are applied to a sufficient thickness such that the entire coating does not dissolve in the gastrointestinal fluids. In some embodiments of the invention, the enteric coating material of the oral dosage form contains a methacrylic acid copolymer. More particularly, the enteric coating of an oral dosage form of the invention is an aqueous dispersion of anionic polymers with methacrylic acid as a functional group like the product sold as Eudragit© L30D-55 (Evonik Industries). The enteric coating of an oral dosage form of the invention may also include a plasticizer, such as triethyl citrate, an anti-tacking agent, such as talc, and a diluent.

As stated above, proliposomal powder dispersions and oral dosage forms of the invention may be used in methods for treating individuals for conditions and disorders associated with, or caused by low blood plasma levels of endogenous testosterone. Low endogenous testosterone refers to a sub-physiological testosterone level. In humans, a low blood plasma level of endogenous testosterone is commonly considered to be 300 ng/dL (testosterone/plasma), or less. Accordingly, an oral dosage form of the invention may be used therapeutically to raise an individual's plasma concentration of testosterone to at least 300 ng/dL, at least 350 ng/dL, a least 400 ng/dL, at least 450 ng/dL, at least 500 ng/dL, at least 550 ng/dL, at least 600 ng/dL, at least 650 ng/dL, at least 700 ng/dL, at least 750 ng/dL, at least 800 ng/dL, at least 850 ng/dL, at least 900 ng/dL, at least 950 ng/dL, at least 1000 ng/dL, at least 1050 ng/dL, or any plasma testosterone level therein. The administration of some oral dosage forms of the invention to an individual in need thereof raise plasma levels to any one of the aforementioned plasma levels within five hours after administration under fasting or fed conditions.

A method of the invention for treating an individual to raise low endogenous levels of testosterone may be, in some methods, be referred to as a testosterone replacement therapy (TRT). Examples of conditions and disorders that may be treated by administering an oral dosage form of the invention include, but are not limited to Low endogenous testosterone levels can result from consequences of injury, infection, loss of testicles, chemotherapy, radiation treatment, genetic abnormalities, hemochromatosis, dysfunction of the pituitary gland, inflammatory disease, medication side effect, chronic kidney failure, liver cirrhosis, stress, alcoholism, obesity, Kallman's syndrome, idiopathic gonadotropin deficiency, Klinefelter's syndrome, pituitary hypothalamus injury due to tumours, osteoporosis, diabetes mellitus, chronic heart failure, chemotherapy, hemochromatosis, cirrhosis, renal failure, AIDS, sarcoidosis, Kallman's Syndrome, androgen receptor defects, 5-alpha reductase deficiency, myotonic dystrophy, cryptorchidism, mumps orchitis, aging, fertile eunuch syndrome, and pituitary disorders. Another disorder that is associated with low endogenous plasma levels of testosterone disorder is male hypogonadism, a disorder which may also be referred to as testosterone deficiency syndrome (TDS). Hypogonadism results from a failure of the testes to produce adequate androgen.

Individuals with low levels of circulating testosterone may experience symptoms such as, but not limited to, fatigue, erectile dysfunction, and body composition changes. The cause of low endogenous testosterone levels may be primary (genetic anomaly, Klinefelter's syndrome) or secondary (defect in hypothalamus or pituitary), but often presents with the same symptomatology. In older patients, androgen deficiency of the aging male (ADAM) is an important cause of secondary hypogonadism because testosterone levels decline progressively after age 40. Hypogonadal patients have alterations not only in sexual function and body composition, but also in cognition and metabolism. Regardless of etiology, hypogonadal patients who are both symptomatic and who have clinically significant alterations in laboratory values are candidates for treatment.

achieved on a C18; 150×4.6 mm (5 μm) (Ace) column. The mobile phase flow rate was set at 1.4 mL/min. while the column temperature was maintained at 40° C. The total run time was 15 minutes with injection volume of 35 μl. The testosterone was detected using a UV detector at absorbance maxima of 243 nm. The retention time of testosterone was found to be around 10 minutes. The method was able to resolve testosterone undecanoate and all other excipients. The solubility data are reported in FIG. 1.

TABLE 1

| Formulation Components | Formulations | | | | |
| --- | --- | --- | --- | --- | --- |
| | TSX-011 | TSX-048 | TSX-049 | TSX-056 | TSX-057 |
| Lipid | DSPC | DMPC | DPPC | MPPC | DPPC + OA |
| Drug:Lipid ratio | 1:2 | 1:3 | 1:2 | 1:3 | 1:2 |
| TU (mg) | 31.6 | 25 | 25 | 25 | 25 |
| Lipid (mg) | 63.2 | 75 | 50 | 75 | 43.5 |
| Na Starch Glycolate | 6.1 mg | — | — | — | — |
| Oleic acid | — | — | — | — | 6.5 mg |
| Microcrystalline Cellulose | 100.8 mg | — | — | — | — |
| Mannitol | — | 125 mg | 93.75 mg | 125 mg | 93.8 mg |
| Capsule | Vcaps ® Plus enteric coated (size "1") | Vcaps ® enteric (Size '0') | Vcaps ® enteric (Size '0') | Vcaps ® enteric (Size '0') | Vcaps ® enteric (Size '0') |
| Capsule fill weight (mg) | 201.7 | 225 | 150 | 150 | 150 |
| TU (mg/caps) | 31.6 | 24.1 | 22.81 | 14.56 | 22.05 |

Composition of Formulation Candidates.

Some oral dosage forms of the invention may be administered to deliver, for example, 96 to 1,580 mg/day, which is the equivalent of about 60.75 to 1000 mg of testosterone/day. In certain embodiments of the invention, a daily dose of TU that may be administered to an adult human via an oral dosage form of the invention is about 95 mg TU/60 kg body weight, about 192 mg/60 kg body weight, about 384 mg/60 kg body weight, about 768 mg/60 kg body weight, about 1,152 mg/60 kg body weight, or any dose therein.

EXAMPLES

Figure 2:
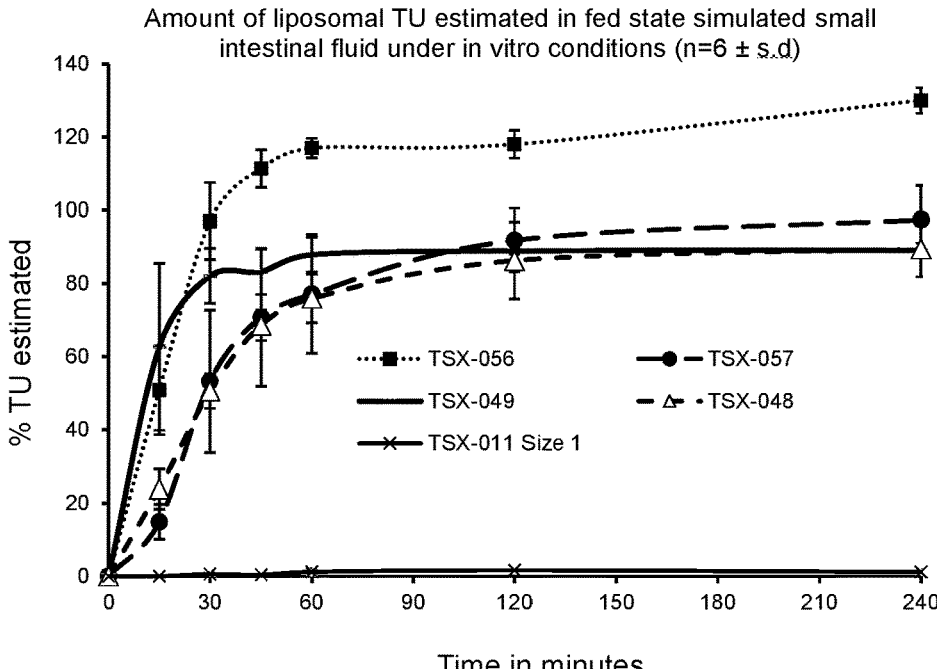
FIG. 2 shows the % amount of TU released from the following capsules containing TU proliposomal powder dispersion formulations over time in simulated small intestinal fluid fed state: TSX-011 (TU:DSPC=1:2); TSX-048 (TU:DMPC=1:3); TSX:049 (TU:DPPC=1:2); TSX-056 (TU:MPPC=1:3); and TSX-057 (TU:DPPC+Oleic Acid=1:2). n=6/capsule formulation.

Example 1. In-vitro testing of TU proliposomal powder dispersion formulation candidates: TU release in phosphate buffer (pH 6.8). The percentage of TU released over time into a phosphate buffer solution (pH 6.8) was determined for the following encapsuled TU proliposomal powder dispersion formulations: TSX-011; TSX-048; TSX:049; TSX-056; and TSX-057. n=3 for TSX-011 and TSX-048. n=6 for TSX-049, TSX-056, and TSX-057. The compositions for each of the tested formulations are described in Table 1. To perform the solubility assays, one capsule, each was added to 250 ml of 0.2M tribasic sodium phosphate with containing 1% w/v SLS was added. The final concentration of SLS in the combined media was 0.25% w/v. The pH of the media was adjusted 6.8 with 2N HCl or 2N NaOH, and dissolution conditions were maintained at 37±0.5° C. for 4 hours at 75 RPM. Sample aliquots were collected at 0, 15, 30, 60, 90, 120, and 240 minutes, and filtered using 5μ glass fiber filter, and then estimated, using high pressure liquid chromatography (HPLC). HPLC analysis was carried out using a gradient method. The mobile phase consisted of water and acetonitrile as follows: (90% water+10% acetonitrile) at 0 minutes; (4% water+96% acetonitrile) at 2 minutes; and (4% water+96% acetonitrile) at 15 minutes. Separation was Example 2. In-vitro testing of TU proliposomal powder dispersion formulation candidates: TU release in simulated small intestinal fluid fed state. The percentage of TU released over time into a 0.1 N HCl solution was determined for the following encapsuled TU proliposomal powder dispersion formulations: TSX-011; TSX-048; TSX:049; TSX-056; and TSX-057. n=6 for each formulation. The compositions for each of the tested formulations are described in Table 1. The 0.1 N HCl dissolution media simulates a fed state in small intestine fluid. Dissolution of each capsule was carried out in 750 mL of 0.1 N HCl, and maintained at 37±0.5° C. for 4 hours at 75 RPM. Sample aliquots were collected at 0, 15, 30, 60, 90, 120, and 240 minutes, and filtered using 5μ glass fiber filter, and then estimated, using HPLC as described in Example 1. The solubility data are reported in FIG. 2.

Example 3. Single dose study design to assess dose response rates in female dogs. Dose response rates were assessed for TSX-011; TSX-048; TSX:049; TSX-056; and TSX-057 in dogs. Each formulation was orally administered to female beagle dogs under fasted conditions. The compositions of the administered formulations are described in Table 1. To perform the studies, the dogs were fasted overnight, dosing (oral administration of 1 capsule/formulation/dog) was performed the subsequent morning. The formulation dose for each formulation was normalized based on the weight of each dog (mg of administered formulation/kg of body weight). See Table 2.

TABLE 2

| | Formulation dose normalized (administered per kg body weight) of dog | | | | | |
|---|---|---|---|---|---|---|
| Animal ID | Average dog b.w (kg) | TSX-011 (mg/kg b.w) | TSX-048 (mg/kg b.w) | TSX-049 (mg/kg b.w) | TSX-056 (mg/kg b.w) | TSX-057 (mg/kg b.w) |
| 1F1:3402089 | 10.5 | 3.0 | 2.3 | 2.2 | 1.4 | 2.1 |
| 1F2:3614892 | 9.5 | 3.3 | 2.5 | 2.4 | 1.5 | 2.3 |
| 1F3:3383998 | 8.5 | 3.7 | 2.8 | 2.7 | 1.7 | 2.6 |
| 1F4:3401473 | 11.5 | 2.7 | 2.1 | 2.0 | 1.3 | 1.9 |
| 1F5:3404286 | 9.8 | 3.2 | 2.5 | 2.3 | 1.5 | 2.3 |
| 1F6:3567592 | 9.8 | 3.2 | 2.5 | 2.3 | 1.5 | 2.3 |

Blood samples were taken from each dog by venipuncture of the jugular vein at 1 one hour before oral administration, and then at 2, 4, 6, 8, 12, 15, 18, 21 and 24 hours post-administration.

Figure 3A:
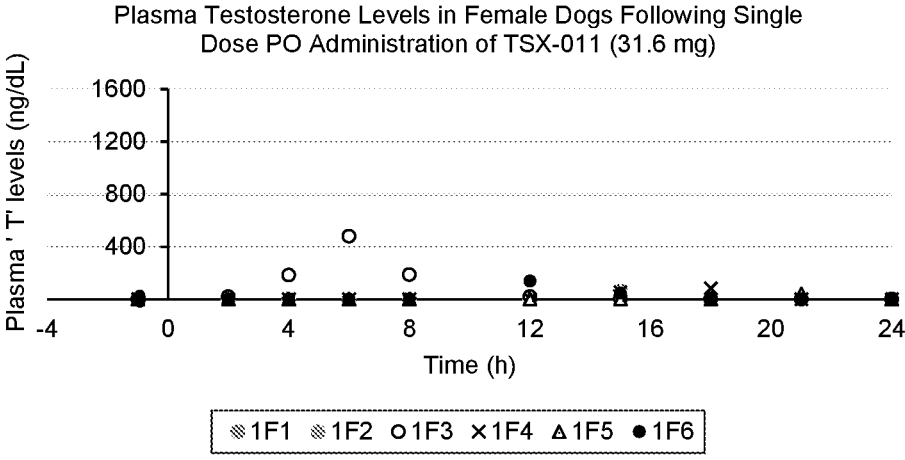
FIG. 3A shows plasma T levels in six fasted dogs following single dose post-oral administration of a TSX-011 capsule (31.6 mg TU, TU:DSPC=1:2).
Figure 3B:
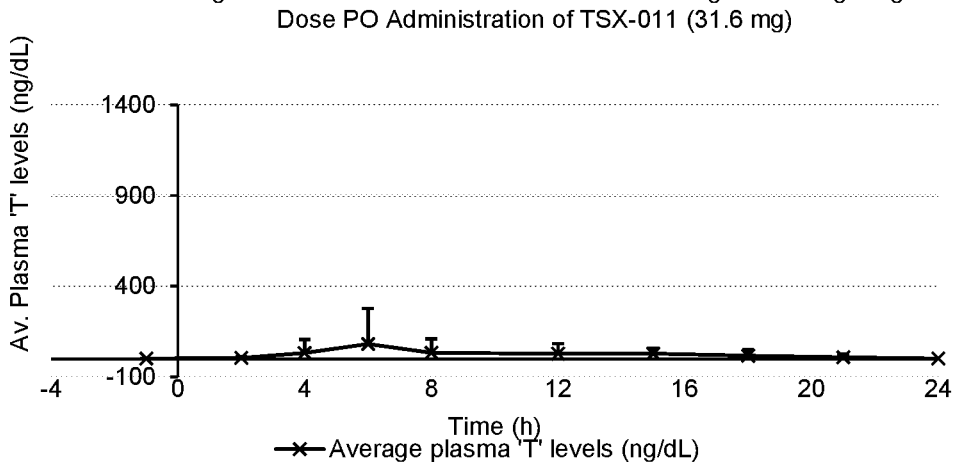
FIG. 3B shows the average plasma T levels over time, based on the individual data points in FIG. 3A.
Figure 4A:
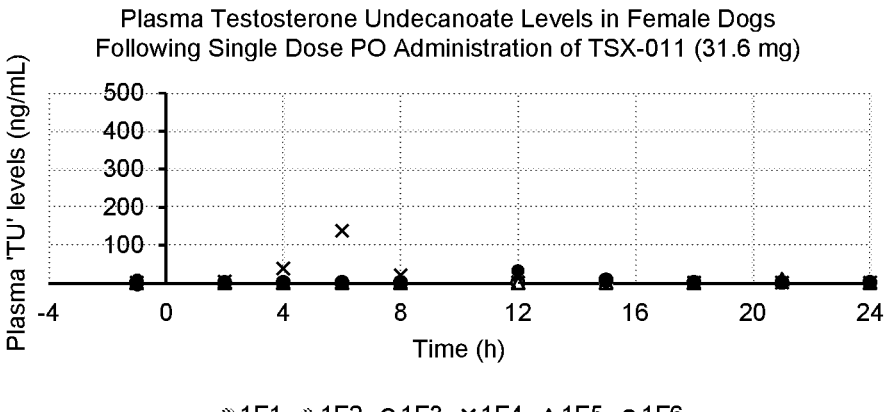
FIG. 4A shows plasma TU levels of the six fasted dogs described in FIG. 3A for the TSX-011 formulation.
Figure 4B:
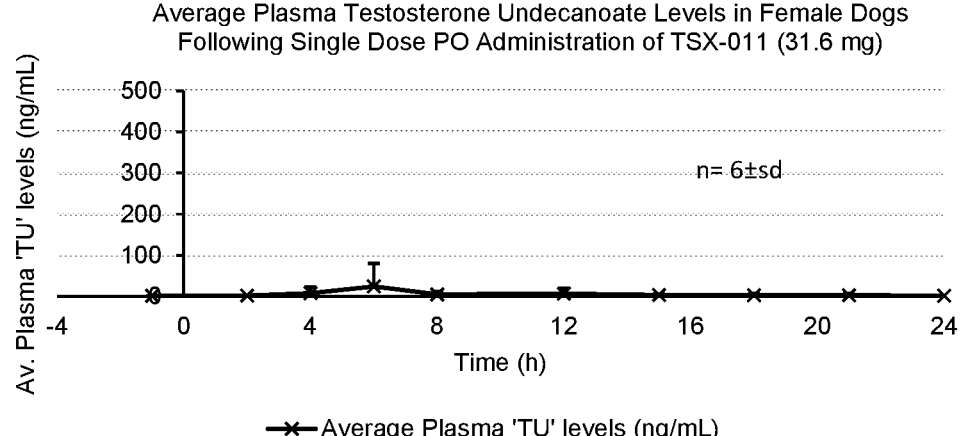
FIG. 4B shows the average plasma TU levels over time, based on the individual data points in FIG. 4A.

Example 4. Plasma T and TU levels were determined in blood samples obtained from fasted dogs following a single dose administration of TSX-011, as described in Example 3. Plasma T and TU levels, respectively, for each dog over time are shown in FIGS. 3A and 4A. FIGS. 3B and 4B show the average plasma T and TU levels over time. Average $t_{max}$ (h) for plasma T levels was $12\pm7.82$. Average $C_{max}$ (ng/dL) for T levels was $135\pm176$.

Figure 5A:
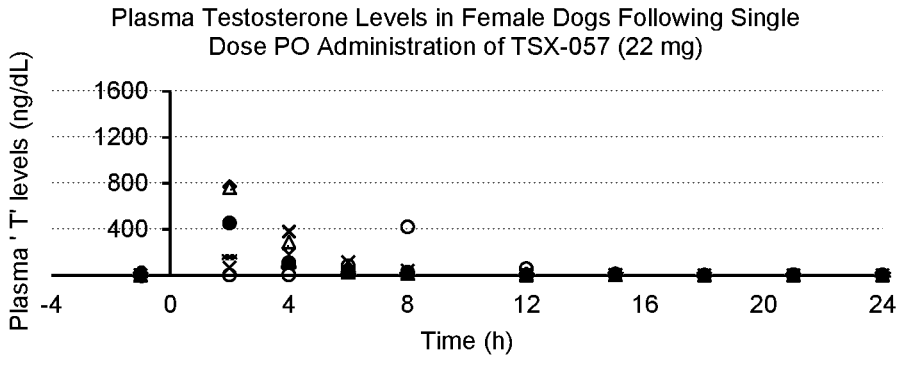
FIG. 5A shows plasma T levels in six fasted dogs following single dose post-oral administration of a TSX-057 capsule (22 mg TU, TU:(DPPC+Oleic Acid)=1:2).
Figure 5B:
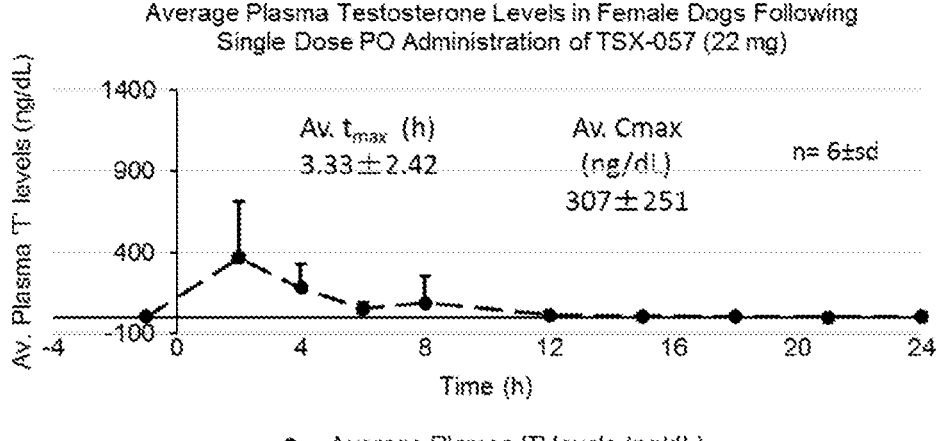
FIG. 5B shows the average plasma T levels over time, based on the individual data points in FIG. 5A.
Figure 6A:
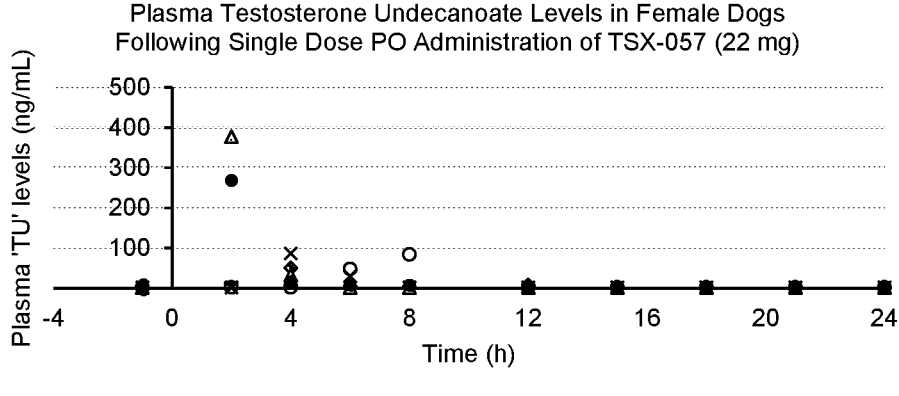
FIG. 6A shows plasma TU levels of the six fasted dogs described in FIG. 5A for the TSX-057 formulation.
Figure 6B:
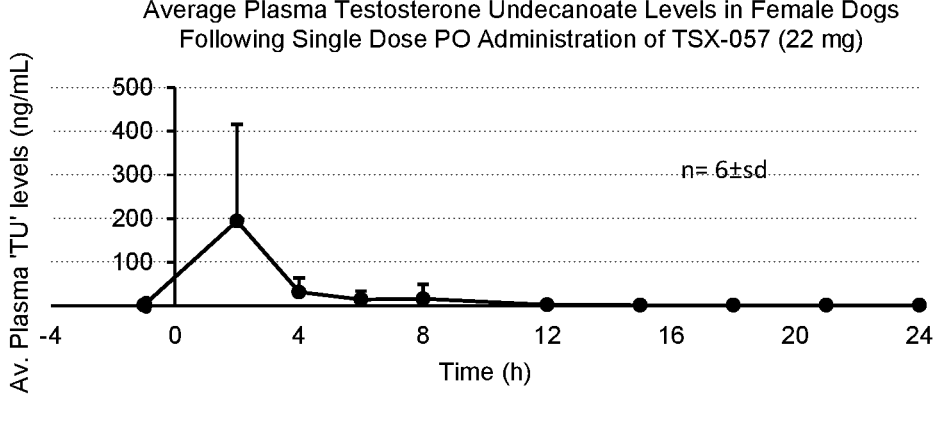
FIG. 6B shows the average plasma TU levels over time, based on the individual data points in FIG. 5A.

Example 5. Plasma T and TU levels were determined in blood samples obtained from fasted dogs following a single dose administration of TSX-057, as described in Example 3. Plasma T and TU levels, respectively, for each dog over time are shown in FIGS. 5A and 6A. FIGS. 5B and 6B show the average plasma T and TU levels over time. Average $t_{max}$ (h) for plasma T levels was $3.33\pm2.42$. Average $C_{max}$ (ng/dL) for T levels was $307\pm251$.

Figure 7A:
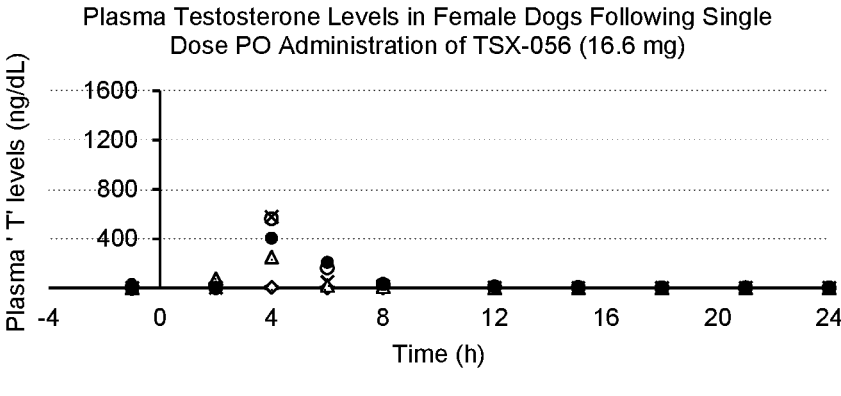
FIG. 7A shows plasma T levels in six fasted dogs following single dose post-oral administration of a TSX-056 capsule (16.6 mg TU, TU:MPPC=1:3).
Figure 7B:
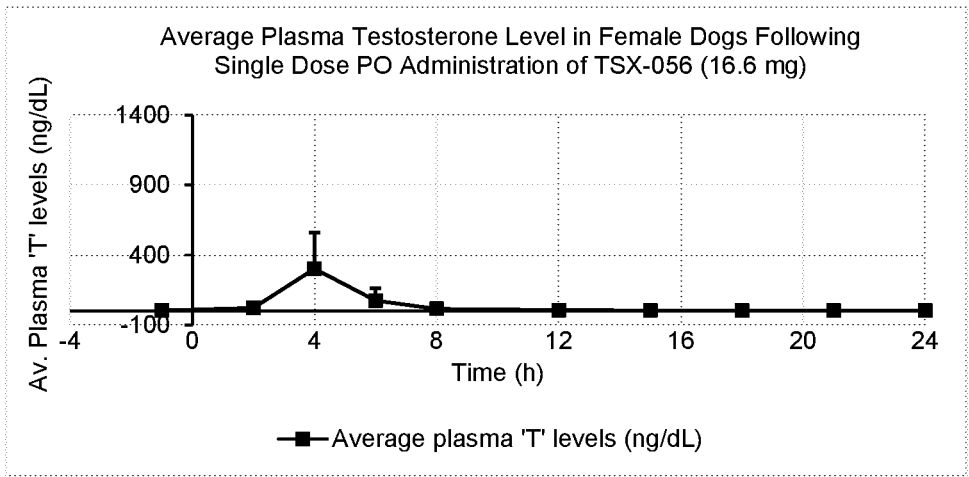
FIG. 7B shows the average plasma T levels over time, based on the individual data points in FIG. 7A.
Figure 8A:
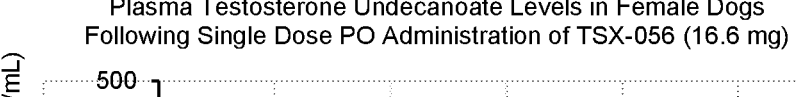
FIG. 8A shows plasma TU levels of the six fasted dogs described in FIG. 7A for the TSX-056 formulation.
Figure 8A:
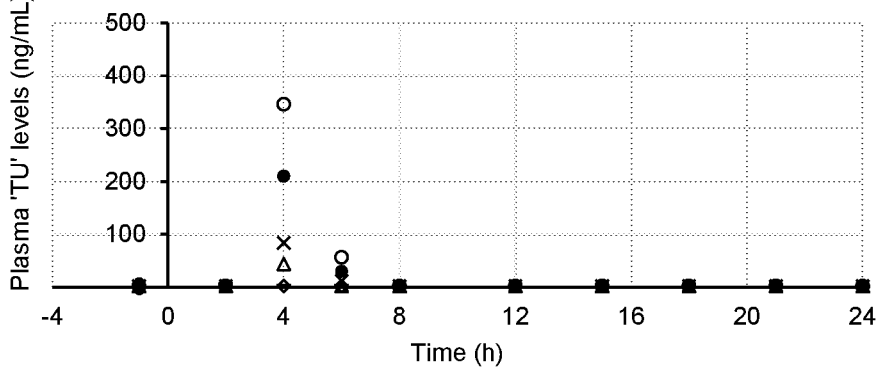
Figure 8B:
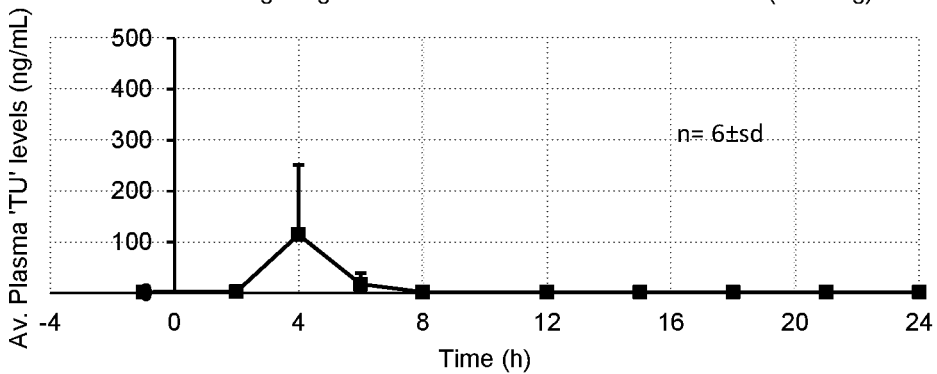
FIG. 8B shows the average plasma TU levels over time, based on the individual data points in FIG. 7A.

Example 6. Plasma T and TU levels were determined in blood samples obtained from fasted dogs following a single dose administration of TSX-056, as described in Example 3. Plasma T and TU levels, respectively, for each dog over time are shown in FIGS. 7A and 8A. FIGS. 7B and 8B show the average plasma T and TU levels over time. Average $t_{max}$ (h) for plasma T levels was $3.33\pm1.33$. Average $C_{max}$ (ng/dL) for T levels was $306.6\pm251.16$.

Figure 9A:
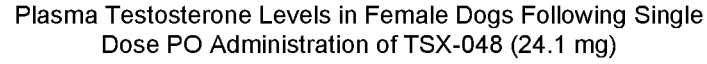
FIG. 9A shows plasma T levels in six fasted dogs following single dose post-oral administration of a TSX-048 capsule (24.1 mg TU, TU:DMPC=1:3).
Figure 9A:
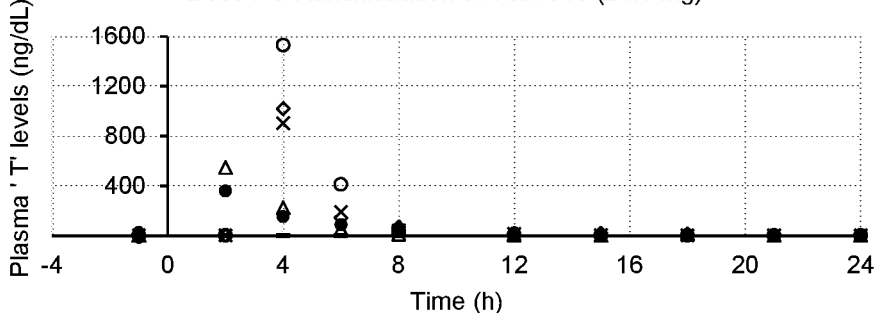
Figure 9B:
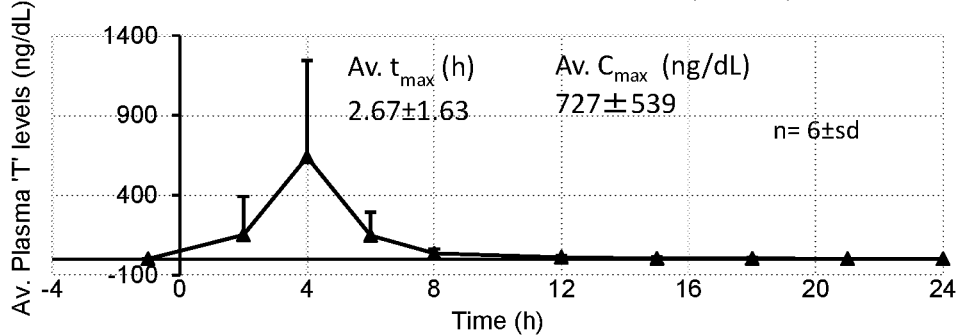
FIG. 9B shows the average plasma T levels over time, based on the individual data points in FIG. 9A.
Figure 10A:
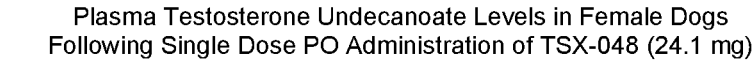
FIG. 10A shows plasma TU levels of the six fasted dogs described in FIG. 9A for the TSX-048 formulation.
Figure 10A:
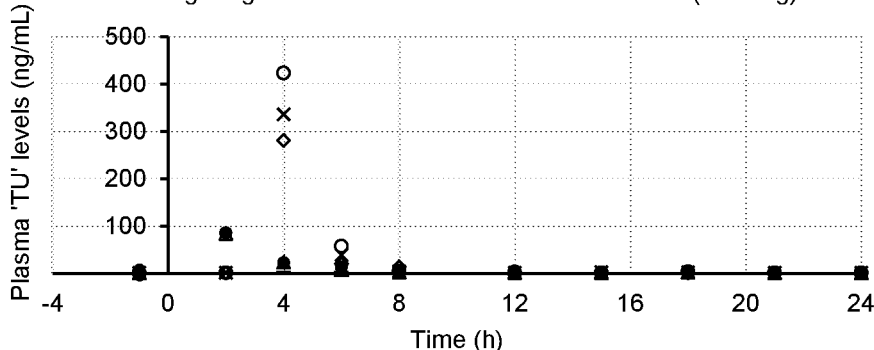
Figure 10B:
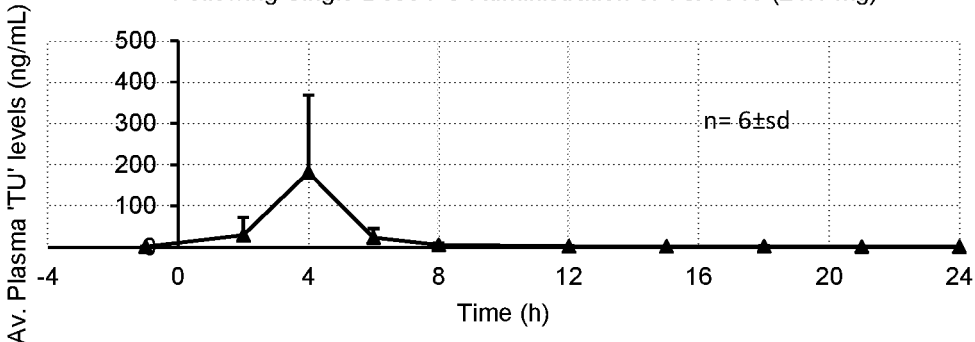
FIG. 10B shows the average plasma TU levels over time, based on the individual data points in FIG. 9A.

Example 7. Plasma T and TU levels were determined in blood samples obtained from fasted dogs following a single dose administration of TSX-048, as described in Example 3. Plasma T and TU levels, respectively, for each dog over time are shown in FIGS. 9A and 10A. FIGS. 9B and 10B show the average plasma T and TU levels over time. Average $t_{max}$ (h) for plasma T levels was $2.67\pm1.63$. Average $C_{max}$ (ng/dL) for T levels was $727\pm539$.

Figure 11A:
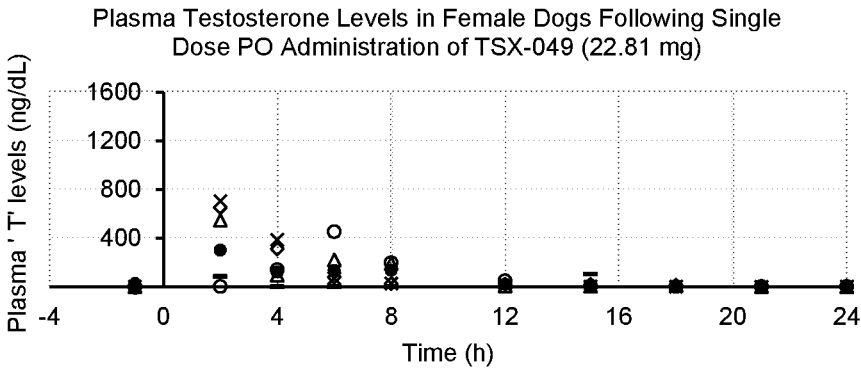
FIG. 11A shows plasma T levels in six fasted dogs following single dose post-oral administration of a TSX-049 capsule (22.81 mg TU, TU:DPPC=1:2).
Figure 11B:
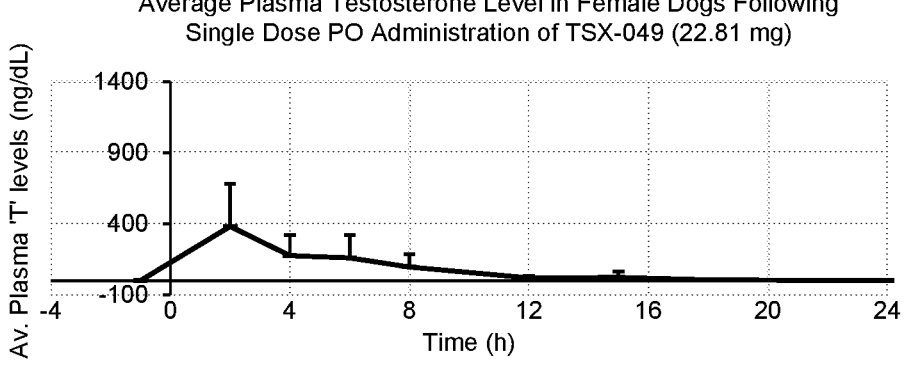
FIG. 11B shows the average plasma T levels over time, based on the individual data points in FIG. 11A.
Figure 12A:
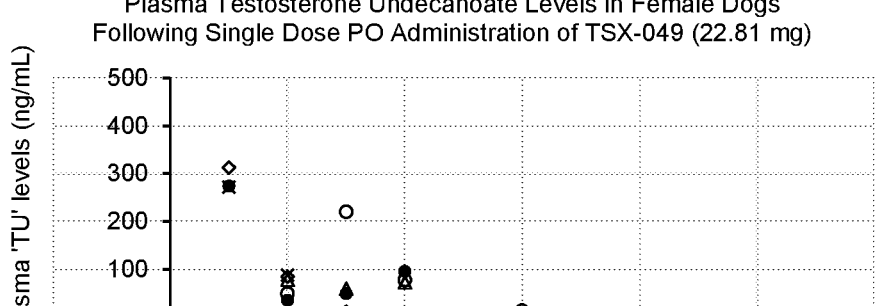
FIG. 12A shows plasma TU levels of the six fasted dogs described in FIG. 11A for the TSX-049 formulation.
Figure 12B:
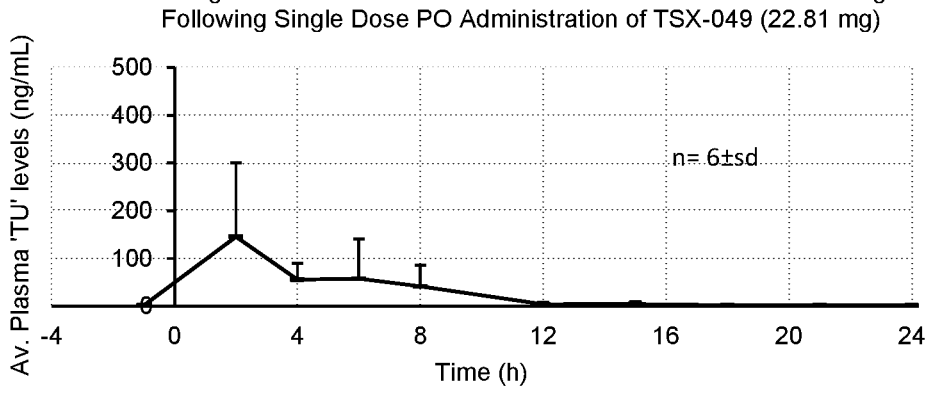
FIG. 12B shows the average plasma TU levels over time, based on the individual data points in FIG. 11A.

Example 8. Plasma T and TU levels were determined in blood samples obtained from fasted dogs following a single dose administration of TSX-048, as described in Example 3. Plasma T and TU levels, respectively, for each dog over time are shown in FIGS. 11A and 12A. FIGS. 11B and 12B show the average plasma T and TU levels over time. Average $t_{max}$ (h) for plasma T levels was $4.83\pm5.23$. Average $C_{max}$ (ng/dL) for T levels was $461\pm226$.

Figure 13:
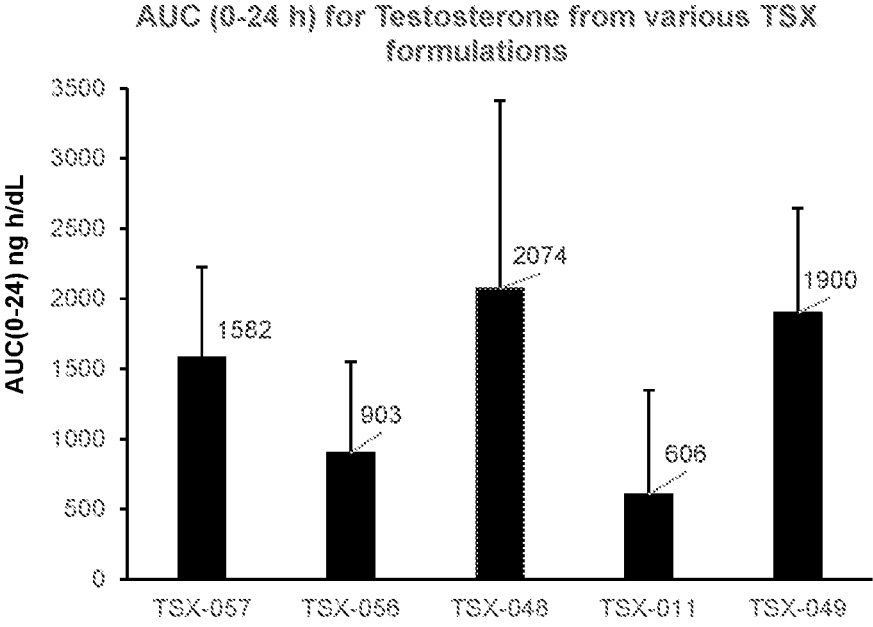
FIG. 13 shows the AUC (ng h/dL) for T over a 24 hour period following oral administration to fasted female dogs of a single dose of: a TSX-011 capsule (31.6 mg TU, TU:D-SPC=1:2); a TSX-057 capsule (22 mg TU, TU:(DPPC+Oleic Acid)=1:2); a TSX-056 capsule (16.6 mg TU, TU:MPPC=1:3); a TSX-048 capsule (24.1 mg TU, TU:DMPC=1:3); and a TSX-049 capsule (22.81 mg TU, TU:DPPC=1:2), respectively. (n=6)
Figure 14:
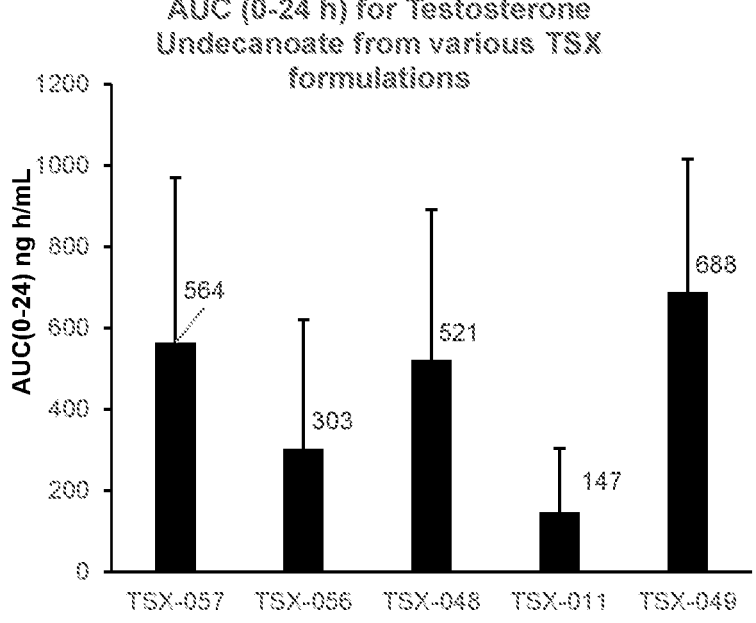
FIG. 14 shows the AUC (ng h/dL) for TU over a 24 hour period in the dogs described for FIG. 13.

Example 9. The AUC (ng h/dL) for T and TU were determined for TSX-011; TSX-048; TSX:049; TSX-056; and TSX-057, based on the 24 hour, single dose, fasted dog study described in Examples 3-8. AUC data are reported in FIGS. 13 and 14. Table 3 contains the T AUC values for each formulation and individual dog in the study. The T and TU AUC values for TSX-048 were the highest among the tested formulations; however, the AUC values for TSX-049 were also good, but demonstrated lower variability. The composition of the TSX-057 formulation includes the components of the TSX-049, plus oleic acid. The AUC values for TSX-057 demonstrated that the inclusion of oleic acid did not result in a significant improvement. These studies also showed that the AUC values for TU were about 25%-33% of the T AUC values, thereby demonstrating good absorption of TU.

TABLE 3

| | Testosterone $AUC_{0-24}$, ng h/dL | | | | |
|---|---|---|---|---|---|
| | TSX-057 | TSX-056 | TSX-048 | TSX-011 | TSX-049 |
| | | | Dose | | |
| Animal ID | 22 mg | 16.6 mg | 24.1 mg | 31.6 mg | 22.8 mg |
| 1F1 | 615.99 | 179.24 | 45.6 | 45.6 | 524.5 |
| 1F2 | 2310.74 | 120.39 | 2727.38 | 241.05 | 2356.58 |
| 1F3 | 1699.87 | 1618.35 | 4037.32 | 2047.93 | 1991.51 |
| 1F4 | 1321.4 | 1351.08 | 2394.99 | 452.58 | 2487.16 |
| 1F5 | 2247.4 | 761.79 | 1760.11 | 168.3 | 2411.95 |
| 1F6 | 1299.3 | 1384.79 | 1477.1 | 677.75 | 1629.95 |
| Mean | 1582.46 | 902.60 | 2073.75 | 605.54 | 1900.28 |
| SD | 643.24 | 648.21 | 1338.19 | 741.17 | 746.81 |
| Geomean | 1451.10 | 606.50 | 1209.23 | 324.24 | 1699.19 |

ANOVA: Based on geometric mean, no differences among all formulations. However, animal 1F1 is virtually a non-responder for all formulations. If excluded, then there are significant differences between the formulations with respect to AUC.

Figure 15:
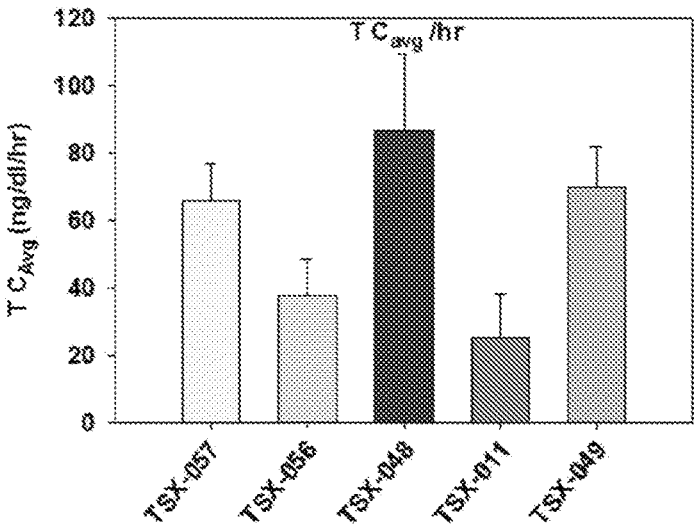
FIG. 15 shows the $C_{avg}$ (ng/dL) for T over a 24 hour period in the dogs described for FIG. 13.
Figure 16:
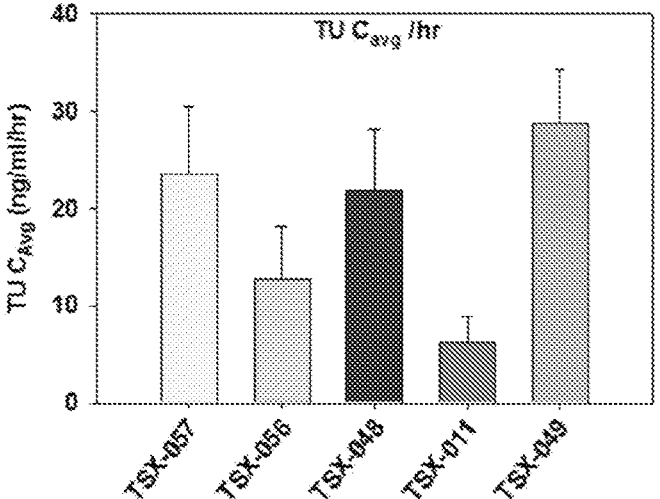
FIG. 16 shows the $C_{avg}$ (ng/dL) for TU over a 24 hour period in the dogs described for FIG. 13.

Example 10. The steady state average concentration $C_{avg}$ (ng/dL) for T and TU were determined for TSX-011; TSX-048; TSX:049; TSX-056; and TSX-057, based on the 24 hour, single dose, fasted dog study described in Examples 3-8. $C_{avg}$ data are reported in FIGS. 15 and 16. TSX-048 showed the highest T $C_{avg}$, however TSX-049 showed a good T $C_{avg}$ with lower variability.

Figure 17:
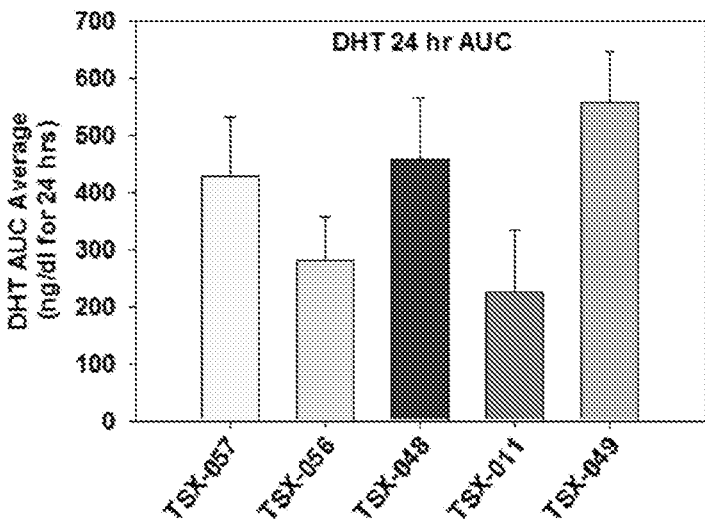
FIG. 17 shows the AUC (ng h/dL) for DHT over a 24 hour period in the dogs described for FIG. 13.
Figure 18:
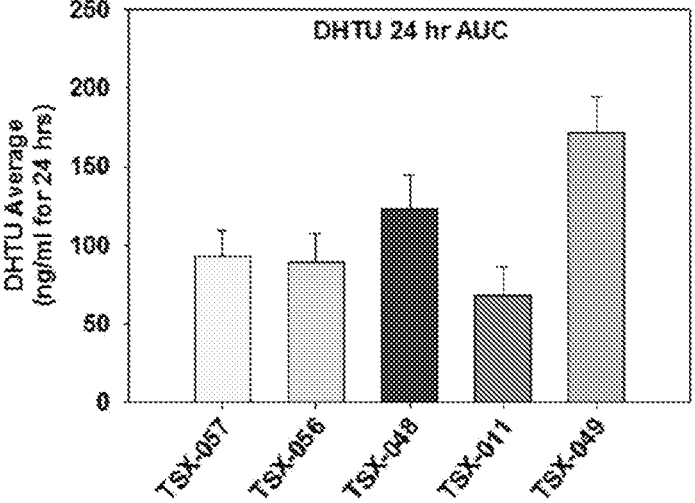
FIG. 18 shows the AUC (ng h/dL) for DHTU over a 24 hour period in the dogs described for FIG. 13.
Figure 19A:
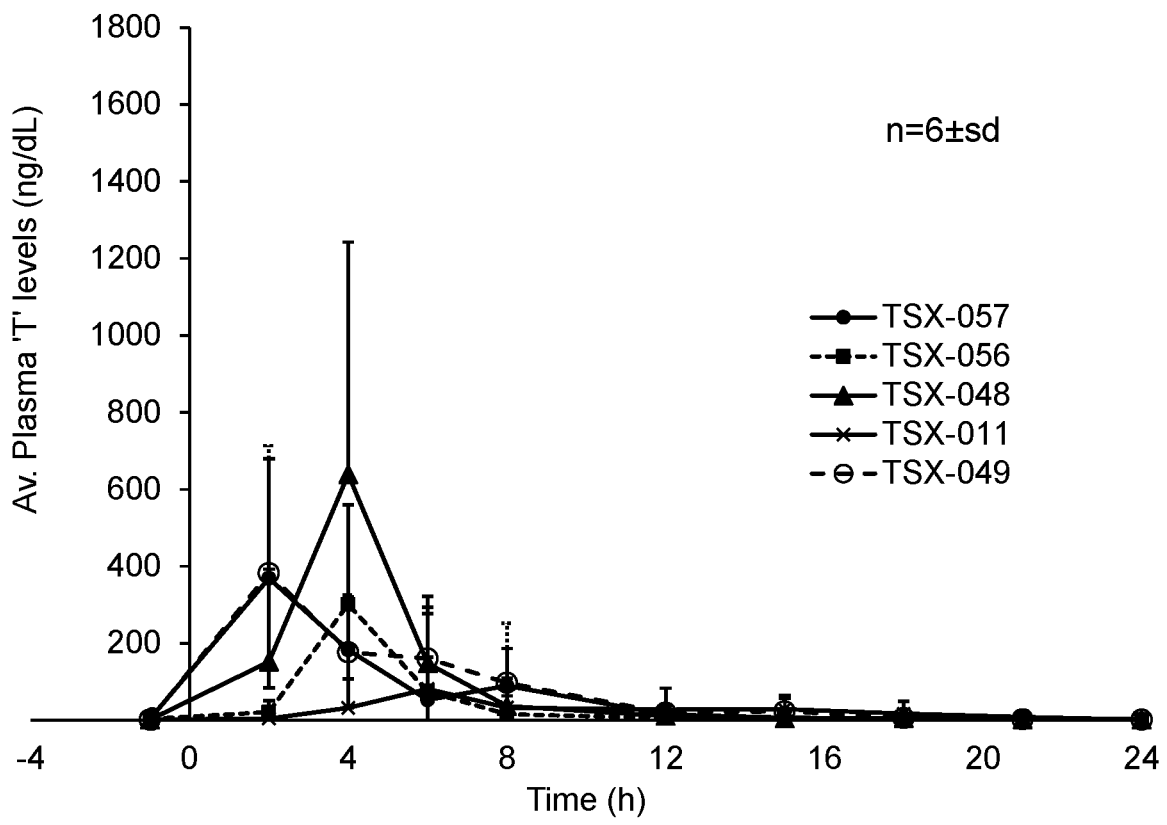
FIG. 19A shows average plasma T levels over a 24 hour period following oral administration to fasted female dogs of a single dose of: a TSX-011 capsule (31.6 mg TU, TU:D-SPC=1:2); a TSX-057 capsule (22 mg TU, TU:(DPPC+Oleic Acid)=1:2); a TSX-056 capsule (16.6 mg TU, TU:MPPC=1:3); a TSX-048 capsule (24.1 mg TU, TU:DMPC=1:3); and a TSX-049 capsule (22.81 mg TU, TU:DPPC=1:2), respectively. (n=6)
Figure 19B:
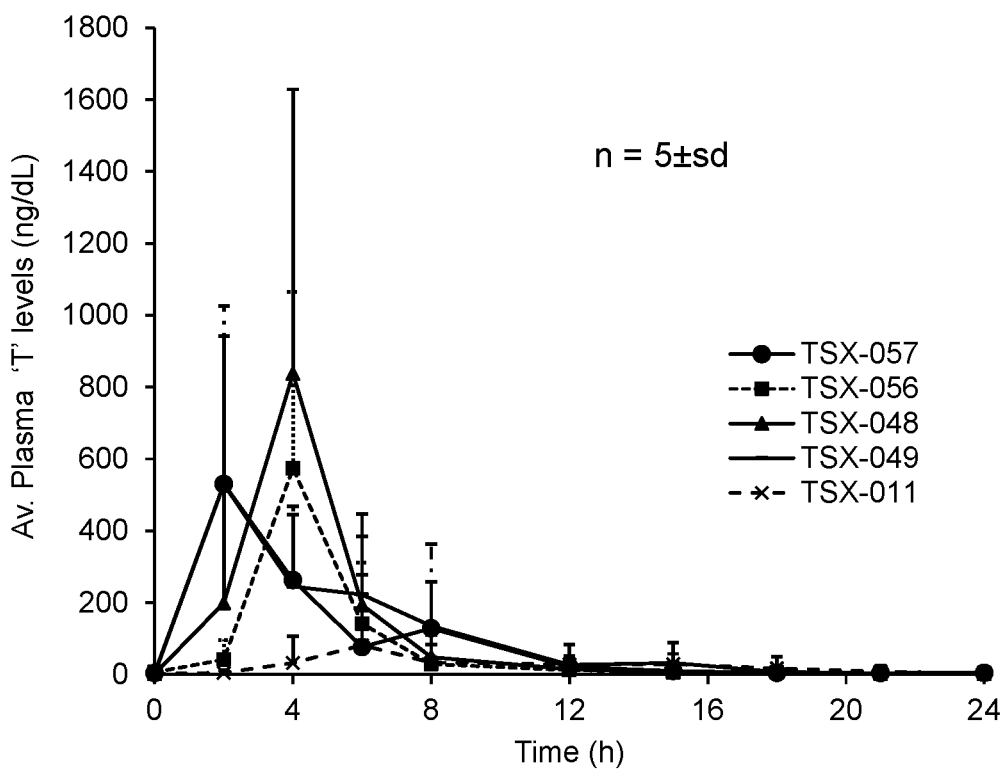
FIG. 19B shows the average plasma T levels of FIG. 19A, which have been normalized to the TSX-011, and with the exclusion of data obtained from dog 1F1. (n=5)

Example 11. The AUC (ng h/dL) for dihydrotestosterone (DHT) and dihydrotestosterone undecanoate (DHTU) were determined for TSX-011; TSX-048; TSX:049; TSX-056; and TSX-057, based on the 24 hour, single dose, fasted dog study described in Examples 3-8. AUC data are reported in FIGS. 17 and 18. DHT and DHTU AUC levels were found to correspond to the T and TU AUC level, demonstrating maintenance of T/DHT and TU/DHTU ratios. All the T/DHT and TU/DHTU ratios were also within the U.S. Food and Drug Administration (FDA)'s guidance of 20. See Table 4.

TABLE 4

| | T:DHT ratio of AUC and $C_{max}$ | | | | | | | | |
|---|---|---|---|---|---|---|---|---|---|
| | T:DHT ratio of AUC | | | | | | | | Excluding dog 1 |
| | Dog 1 | Dog 2 | Dog 3 | Dog 4 | Dog 5 | Dog 6 | Mean | SD | Mean |
| TSX-057 | 3.13 | 3.10 | 3.74 | 1.87 | 7.95 | 6.87 | 4.44 | 2.40 | 4.71 |
| TSX-056 | 2.37 | 1.19 | 2.97 | 2.88 | 3.17 | 5.60 | 3.03 | 1.45 | 3.16 |
| TSX-048 | 1.00 | 3.69 | 8.04 | 4.25 | 5.25 | 3.24 | 4.24 | 2.34 | 4.89 |
| TSX-011 | 1.00 | 3.86 | 2.79 | 2.15 | 3.69 | 2.66 | 2.69 | 1.05 | 3.03 |
| TSX-049 | 1.82 | 3.55 | 2.37 | 3.81 | 4.46 | 4.44 | 3.41 | 1.09 | 3.73 |

| | T:DHT ratio of Cmax | | | | | | | | |
|---|---|---|---|---|---|---|---|---|---|
| | Dog 1 | Dog 2 | Dog 3 | Dog 4 | Dog 5 | Dog 6 | Mean | SD | Mean |
| TSX-057 | 4.28 | 7.50 | 5.00 | 3.53 | 10.30 | 14.28 | 7.48 | 4.15 | 8.12 |
| TSX-056 | 2.43 | 0.88 | 7.65 | 6.08 | 5.29 | 7.98 | 5.05 | 2.85 | 5.58 |
| TSX-048 | 1.00 | 6.62 | 14.85 | 7.64 | 8.82 | 7.22 | 7.69 | 4.44 | 9.03 |
| TSX-011 | 1.00 | 8.51 | 6.57 | 2.08 | 22.53 | 3.06 | 7.29 | 7.99 | 8.55 |
| TSX-049 | 2.30 | 6.16 | 5.03 | 6.97 | 7.77 | 7.21 | 5.91 | 2.01 | 6.63 |

Table 5 compares and summarizes DHT and DHTU, and T and TU pharmacokinetic parameters reported in Examples 3-11 for TSX-011; TSX-048; TSX:049; TSX-056; and TSX-057.

TABLE 5

| Dose | TSX-057 22 mg | TSX-056 16.6 mg | TSX-048 24.1 mg | TSX-011 31.6 mg | TSX-049 22.8 mg |
|---|---|---|---|---|---|
| T | | | | | |
| $AUC_{0-24}$, ng h/dL | 1582 (643) | 903 (648) | 2074 (1338) | 606 (741) | 1900 (747) |
| $C_{max}$, ng/dL | 492 (236) | 307 (251) | 727 (539) | 135 (176) | 461 (226) |
| $C_{min}$, ng/dL | 2.23 (0.57) | 1.9 (0) | 1.9 (0) | 1.9 (0) | 1.9 (0) |
| $t_{max}$, h | 3.33 (2.42) | 3.33 (1.03) | 2.67 (1.63) | 12 (7.82) | 4.83 (5.23) |
| DHT | | | | | |
| $AUC_{0-24}$, ng h/dL | 429 (249) | 280 (191) | 440 (235) | 226 (265) | 559 (205) |
| $C_{max}$, ng/dL | 73 (32) | 48 (33) | 81 (54) | 28 (29) | 76 (28) |
| $C_{min}$, ng/dL | 1.9 (0) | 1.9 (0) | 1.9 (0) | 1.9 (0) | 1.9 (0) |
| $t_{max}$, h | 3.33 (2.42) | 5.33 (3.5) | 2.67 (1.63) | 8.33 (6.95) | 6.83 (4.31) |
| TU | | | | | |
| $AUC_{0-24}$, ng h/dL | 564 (406) | 303 (317) | 521 (370) | 147 (157) | 688 (328) |
| $C_{max}$, ng/dL | 222 (195) | 115 (137) | 202 (168) | 34 (52) | 195 (120) |
| $C_{min}$, ng/dL | 1.9 (0) | 1.9 (0) | 1.9 (0) | 1.9 (0) | 1.9 (0) |
| $t_{max}$, h | 3.33 (2.42) | 3 (1.67) | 2.67 (1.63) | 12 (7.82) | 5.17 (5.08) |
| DHTU | | | | | |
| $AUC_{0-24}$, ng h/dL | 92 (39) | 87 (46) | 122 (53) | 66 (43) | 170 (57) |
| $C_{max}$, ng/dL | 12 (7) | 11 (8) | 16 (12) | 6 (7) | 19 (7) |
| $C_{min}$, ng/dL | 1.9 (0) | 1.9 (0) | 1.9 (0) | 1.9 (0) | 1.9 (0) |
| $t_{max}$, h | 3 (2.1) | 5.33 (3.93) | 3 (2.1) | 2.67 (4.84) | 7.17 (4.12) |

Figure 20:
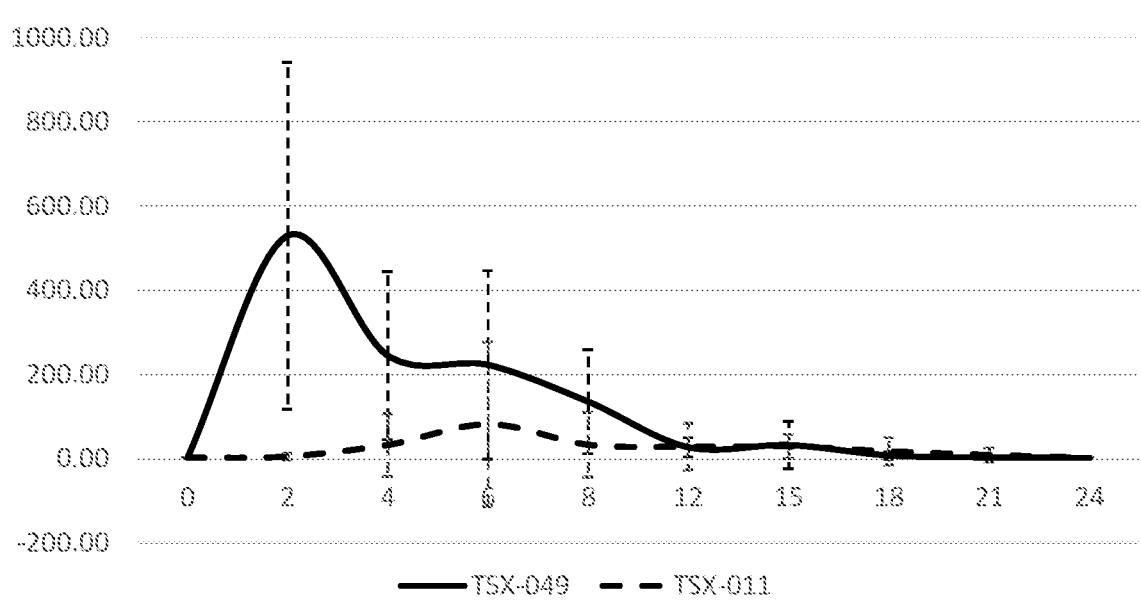
FIG. 20 shows the average plasma testosterone levels in the female dog study following the oral administration of TSX-049 and TSX-011, respectively.
Figure 21A:
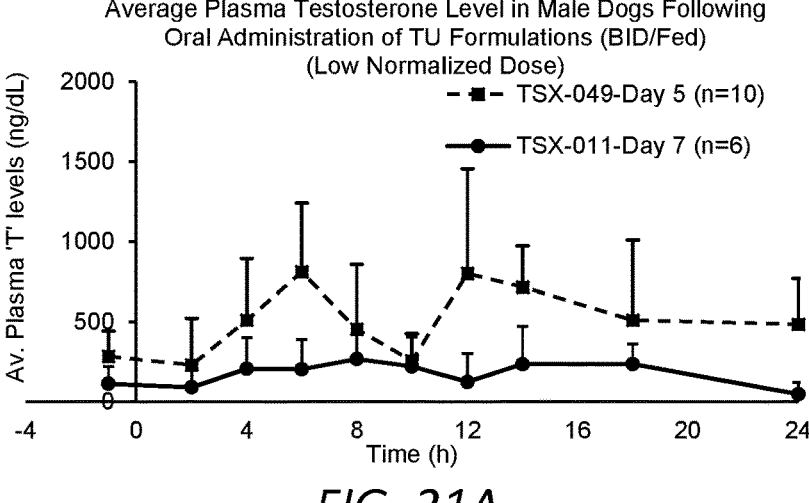
FIG. 21A shows average plasma testosterone levels in male dogs over 24 hours under fed conditions following oral BID administration of a low dose of TU formulated in either TSX-011 capsules (low dose=94.8 mg TU, ratio of TU:D-SPC=1:2) or TSX-049 capsules (low dose=60 mg, ratio of TU:DPPC=1:2).
Figure 21B:
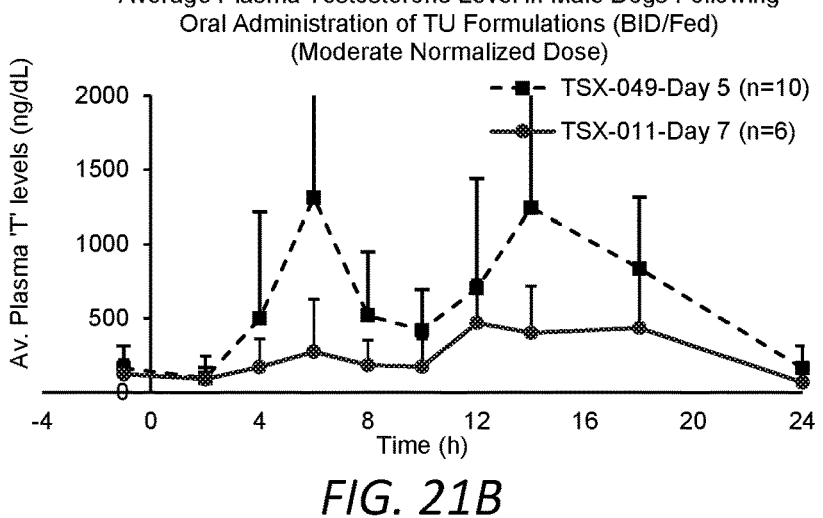
FIG. 21B shows average plasma testosterone levels in male dogs over 24 hours under fed conditions following oral BID administration of a moderate dose of TU formulated in either TSX-011 capsules (moderate dose=189.6 mg TU, ratio of TU:DSPC=1:2) or TSX-049 capsules (low moderate dose=120 mg, ratio of TU:DPPC=1:2).
Figure 21C:
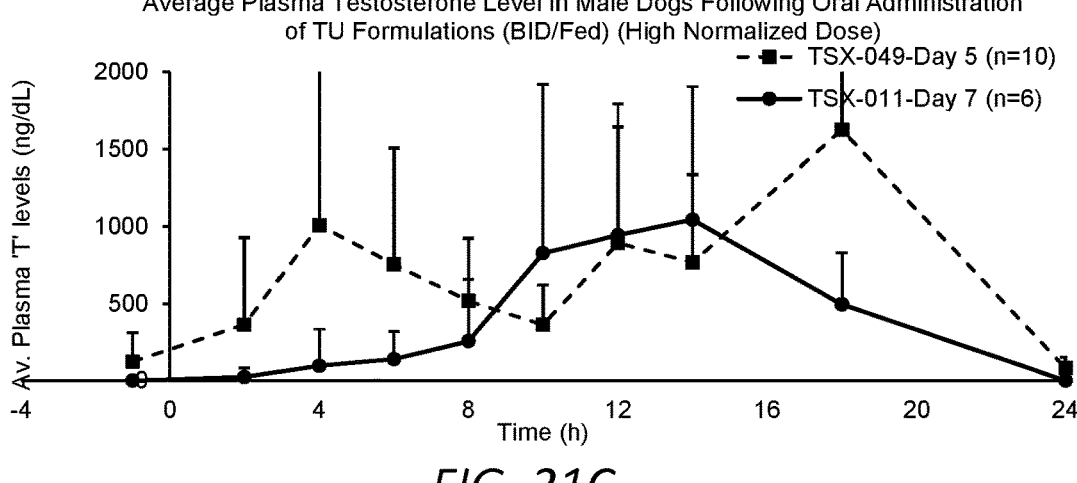
FIG. 21C shows average plasma testosterone levels in male dogs over 24 hours under fed conditions following oral BID administration of a high dose of TU formulated in either TSX-011 capsules (high dose=284.4 mg TU, ratio of TU:D-SPC=1:2) or TSX-049 capsules (high dose=240 mg, ratio of TU:DPPC=1:2).

Table 6 contains pharmacokinetic parameters determined by normalizing the parameters in Table 3 to the administered dosage of TSX-011. Collectively, these data demonstrate that the testosterone PK levels for TSX-049 are superior among the tested formulations, an observation that is brought into view in FIG. 20, which compares the average plasma testosterone levels in the dog study following the oral administration of TSX-049 and TSX-011, respectively.

TABLE 6

| | AUC and $C_{max}$ normalized to the TSX-011 formulation dose (n = 5) | | | | |
|---|---|---|---|---|---|
| Dose | TSX-057 22 mg | TSX-056 16.6 mg | TSX-048 24.1 mg | TSX-011 31.6 mg | TSX-049 22.8 mg |
| | T | | | | |
| $AUC_{0-24}$, ng h/dL | 2551 | 1993 | 3250 | 718 | 3014 |
| $C_{max}$, ng/dL | 801 | 687 | 1143 | 162 | 737 |

15

TABLE 6-continued

AUC and $C_{max}$ normalized to the TSX-011 formulation dose (n = 5)

| Dose | TSX-057 22 mg | TSX-056 16.6 mg | TSX-048 24.1 mg | TSX-011 31.6 mg | TSX-049 22.8 mg |
|---|---|---|---|---|---|
| | DHT | | | | |
| $AUC_{0-24}$, ng h/dL | 682 | 611 | 681 | 262 | 850 |
| $C_{max}$, ng/dL | 115 | 105 | 127 | 34 | 114 |
| | TU | | | | |
| $AUC_{0-24}$, ng h/dL | 951 | 672 | 809 | 167 | 1114 |
| $C_{max}$, ng/dL | 381 | 261 | 317 | 40 | 320 |
| | DHTU | | | | |
| $AUC_{0-24}$, ng h/dL | 145 | 181 | 180 | 70 | 266 |
| $C_{max}$, ng/dL | 20.1 | 22.8 | 24.9 | 6 | 30.5 |

The coefficient of variation (CV %) values for $C_{max}$ and AUC(0-24 h) for the tested formulations indicated that upon dose normalization to TSX-011 and exclusion of the non-responder animal, 1F1, the differences among the formulations were evident. Lower CV % is indicative of lower variation within each formulation for absorption. Among the formulations tested, TSX-049 and TSX-057 showed the lowest CV %. See Table 7 for CV % values determined using results from: the 6 animals in the study, and Table 8 for CV % determination with dog 1F1 excluded.

TABLE 7

CV % of AUC and $C_{max}$ (n = 6)

| Dose | TSX-057 22 mg | TSX-056 16.6 mg | TSX-048 24.1 mg | TSX-011 31.6 mg | TSX-049 22.8 mg |
|---|---|---|---|---|---|
| | T | | | | |
| $AUC_{0-24}$, ng h/dL | 40.6 | 71.8 | 64.5 | 122.3 | 39.3 |
| $C_{max}$, ng/dL | 48 | 81.8 | 74.1 | 130.4 | 49 |
| | DHT | | | | |
| $AUC_{0-24}$, ng h/dL | 58 | 68.2 | 53.4 | 117.3 | 36.7 |
| $C_{max}$, ng/dL | 43.8 | 68.8 | 66.7 | 103.6 | 36.8 |
| | TU | | | | |
| $AUC_{0-24}$, ng h/dL | 72 | 104.6 | 71 | 106.8 | 47.7 |
| $C_{max}$, ng/dL | 87.8 | 119.1 | 83.2 | 152.9 | 61.5 |
| | DHTU | | | | |
| $AUC_{0-24}$, ng h/dL | 42.4 | 52.9 | 43.4 | 65.2 | 33.5 |
| $C_{max}$, ng/dL | 58.3 | 72.7 | 75 | 116.7 | 36.8 |

16

TABLE 8

CV % of AUC and $C_{max}$ (n = 5)

| Dose | TSX-057 22 mg | TSX-056 16.6 mg | TSX-048 24.1 mg | TSX-011 31.6 mg | TSX-049 22.8 mg |
|---|---|---|---|---|---|
| | T | | | | |
| $AUC_{0-24}$, ng h/dL | 40.6 | 71.8 | 64.5 | 122.3 | 39.3 |
| $C_{max}$, ng/dL | 48 | 81.8 | 74.1 | 130.4 | 49 |
| | DHT | | | | |
| $AUC_{0-24}$, ng h/dL | 52.4 | 59.5 | 45.3 | 101.1 | 33.4 |
| $C_{max}$, ng/dL | 40 | 60 | 55.7 | 85.3 | 34.1 |
| | TU | | | | |
| $AUC_{0-24}$, ng h/dL | 61.3 | 89.8 | 60 | 94 | 40.8 |
| $C_{max}$, ng/dL | 73.6 | 100 | 69.4 | 130 | 51.9 |
| | DHTU | | | | |
| $AUC_{0-24}$, ng h/dL | 38.6 | 48.4 | 38.7 | 61.4 | 29.7 |
| $C_{max}$, ng/dL | 50 | 66.7 | 63.2 | 116.7 | 31.8 |

Example 12. The relative in vivo bioavailability of testosterone following the single dose administrations of TSX-011, TSX-048, TSX-049, TSX-056, and TSX-057 in the fasted dog study described in Examples 3-8 was determined for each formulation relative to the bioavailability data determined for TSX-011, and with data obtained from dog 1F1 excluded, based on the bioavailability data reported in Tables 3 and 6. See Table 9.

TABLE 9

| Animal ID # | TSX-057 | TSX-056 | TSX-048 | TSX-011 | TSX-049 |
|---|---|---|---|---|---|
| Dog 2 | 13.77 | 0.95 | 14.84 | 1 | 13.55 |
| Dog 3 | 1.19 | 1.50 | 2.58 | 1 | 1.35 |
| Dog 4 | 4.19 | 5.68 | 6.94 | 1 | 7.62 |
| Dog 5 | 19.18 | 8.62 | 13.71 | 1 | 19.86 |
| Dog 6 | 2.75 | 3.89 | 2.86 | 1 | 3.33 |
| Mean | 8.22 | 4.13 | 8.19 | 1 | 9.14 |
| SD | 7.85 | 3.15 | 5.83 | 0 | 7.60 |

Example 13 Comparison of PK parameters of testosterone in male dogs: TSX-011 vs TSX-049. In view of the strength of its performance in Examples 1-12, with respect to bioavailability and dose response, the TSX-049 formulation (TU:DPPC=1:2) was selected for further pharmacokinetic (PK) studies in male beagle dogs. In these studies TSX-049 was compared to TSX-011 (TU:DSPC=1:2). The TSX-011 formulation is described and characterized in PCT Appl. Pub. No. WO 2017/120592, which is incorporated by reference. The dosage forms of TSX-011 and TSX-049 used in these studies are described in Table 10.

TABLE 10

| Formulation Components | Formulations | |
|---|---|---|
| | TSX-011 | TSX-049 |
| Lipid | DSPC | DPPC |
| Drug:Lipid | 1:2 | 1:2 |

TABLE 10-continued

| Formulation | Formulations | |
| --- | --- | --- |
| Components | TSX-011 | TSX-049 |
| ratio | | |
| TU (mg) | 31.6 | 30 |
| Lipid (mg) | 63.2 | 60 |
| Na Starch Glycolate | 6.1 mg | — |
| Microcrystalline Cellulose | 100.8 mg | — |
| Mannitol | — | 112.5 mg |
| Capsule | Vcaps ® Plus enteric coated | Vcaps ® Plus enteric coated |
| Capsule fill weight (mg) | 201.7 | 202.5 |
| TU (mg/caps) | 31.6 | 30 |

To perform the studies, dogs was were fasted overnight, and fed state dosing was performed the subsequent morning by serving the dogs food immediately after oral dosing, and allowing access to food for 2 hours. A second, oral dose was administered about 8 hours later, again followed by access to food immediately, then for an additional 2 hours. Therefore, dosing was BID. The dogs were administered either low, moderate, or high doses of TU over a 24 hour period of time. For TSX-011, 6 dogs were administered either a low daily TU dose was 94.8 mg, a moderate dose was 189.4 mg, and a high dose was 284.4 mg. For TSX-049, 10 dogs were administered either a low daily TU dose was 60 mg, a moderate dose was 120 mg, and a high dose was 240 mg.

Dosages were normalized based on the weight of each dog (mg of administered TU/kg of body weight). Table 11 summarizes average normalized doses and relative TU dose differences for the low, moderate and high doses in the TSX-011 and TSX-049 groups.

TABLE 11

| TU Dosage Group | Formulation | Dose (mg/kg) | Relative dose difference |
| --- | --- | --- | --- |
| Low dose | TSX-011 vs TSX-049 | 5.9 vs 2.5 | 2.36 |
| Moderate dose | TSX-011 vs TSX-049 | 11.5 vs 5 | 2.3 |
| Higher dose | TSX-011 vs TSX-049 | 17.8 vs 10 | 1.78 |

Figure 22A:
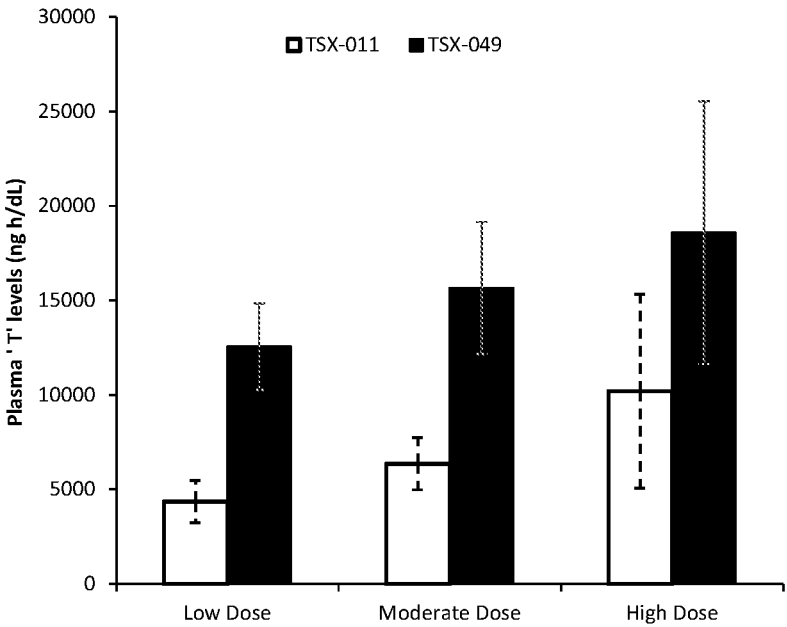
FIG. 22A shows the average AUC (ng h/dL) levels for T over a 24 hour period in fed male dogs following BID administration of low doses, moderate doses, or high doses of TU formulated in TSX-011 capsules (TU:DSPC=1:2) or TSX-049 capsules (TU:DPPC=1:2). (n=6 for TSX-011; n=10 for TSX-049)
Figure 22B:
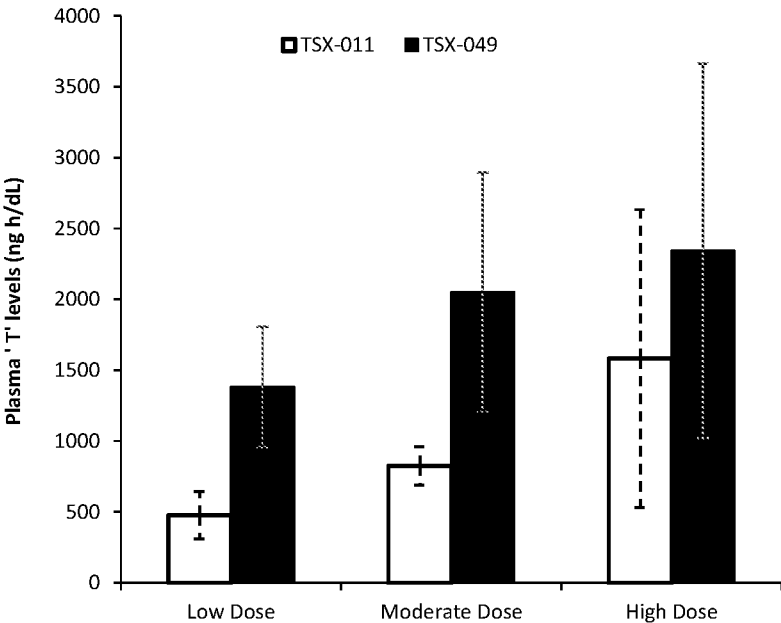
FIG. 22B shows the average $C_{max}$ (ng h/dL) levels for the dog study described in FIG. 21A.

Blood samples were taken from each dog by venipuncture of the jugular vein at 1 one hour before oral administration of the formulations, and then at 2, 4, 6, 8, 12, 15, 18, 21 and 24 hours after administration, and the plasma was collected. PK analysis of the plasma samples included calculating AUC (ng h/dL) and $C_{max}$ (ng h/dL) levels. The AUC and $C_{max}$ data are shown in FIGS. 22A-B, and in Table 12.

TABLE 12

| PK Parameters | TSX-011 | TSX-049 | TSX-049 (x Relative dose difference) |
| --- | --- | --- | --- |
| | Low dose | | |
| $C_{max}$, ng/dL | 476 ± 167 | 585.7 ± 179.2 | 1382.3 ± 422.9 |
| $AUC_{(0-24\ h)}$, ng h/dL | 4349 ± 1118 | 5319 ± 966 | 12552.8 ± 2279.8 |
| | Moderate dose | | |
| $C_{max}$, ng/dL | 825 ± 135 | 892 ± 367 | 2051.6 ± 844.1 |
| $AUC_{(0-24\ h)}$, ng h/dL | 6359 ± 1381 | 6806 ± 1520 | 15658.4 ± 3496 |

TABLE 12-continued

| PK Parameters | TSX-011 | TSX-049 | TSX-049 (x Relative dose difference) |
| --- | --- | --- | --- |
| | Higher dose | | |
| $C_{max}$, ng/dL | 1582 ± 1051 | 1316.2 ± 741.9 | 2342.8 ± 1320.6 |
| $AUC_{(0-24\ h)}$, ng h/dL | 10196 ± 5126 | 10422 ± 3906 | 18586.8 ± 6952.7 |

Relative testosterone bioavailability for was also determined for each dose of TSX-011 and TSX-049, and is reported in Table 13. TSX-049 demonstrated higher bioavailability and a significantly higher dose response in non-hypogonadal male dogs compared to TSX-011.

TABLE 13

| Study | Formulation | Dose (mg)/day | Relative bioavailability (F) |
| --- | --- | --- | --- |
| Low dose | TSX-049 vs TSX-011 | 60 vs 94.8 | 1.93 |
| Moderate dose | TSX-049 vs TSX-011 | 120 vs 189.6 | 1.37 |
| Higher dose | TSX-049 vs TSX-011 | 240 vs 284.4 | 1.21 |

Example 14 Multi-day TSX-049 testosterone undecanoate (TU) dose escalation study in male beagle dogs. To assess the pharmacokinetics of the TSX-049 formulation over an extended time course, and at multiple daily doses of TU, a 40 day dose escalation study was performed using 10 male beagle dogs that were not hypogonadal. For the first 7 days of the study, were not administered the TSX-049 formulation. On day 8 of the study the dogs were orally administered TSX-049 to deliver 30 mg TU BID, daily, for 10 days. On day 18 of the study, the administered daily dose of TU was raised to 60 mg BID and maintained for the next 10 days. On day 28 of the study, administered daily dose of TU was raised to 120 mg BID and maintained through day 38 of the study. The TSX-049 capsules administered in the study are described in Table 10. As each capsule contains a 30 mg dose of TU, multiple TSX-049 capsules were administered as needed to reach the desired daily dosage amount.

Figure 23A:
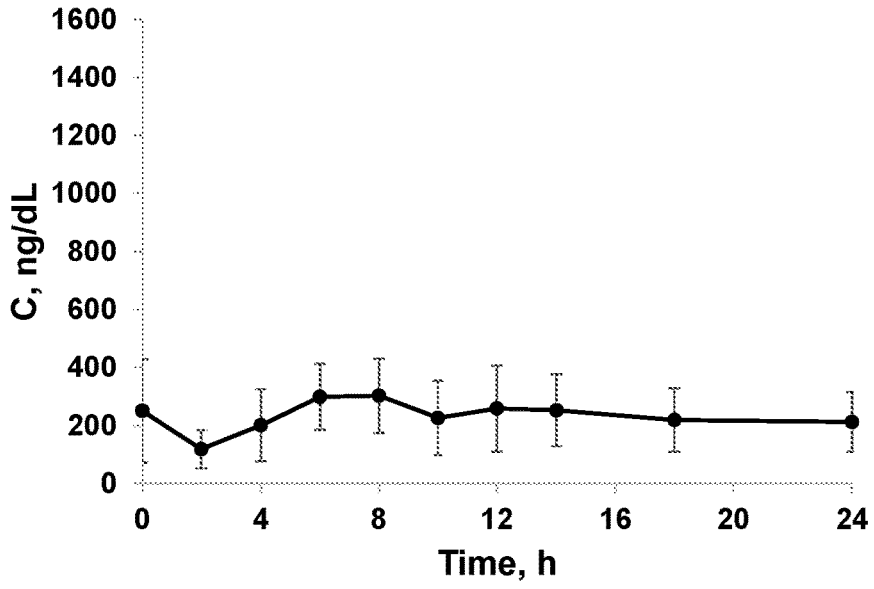
FIG. 23A shows the mean, baseline, pre-dose plasma T concentration over 24 hours in the male dogs used in the multi-day dose escalation study described in Example 14.
Figure 23B:
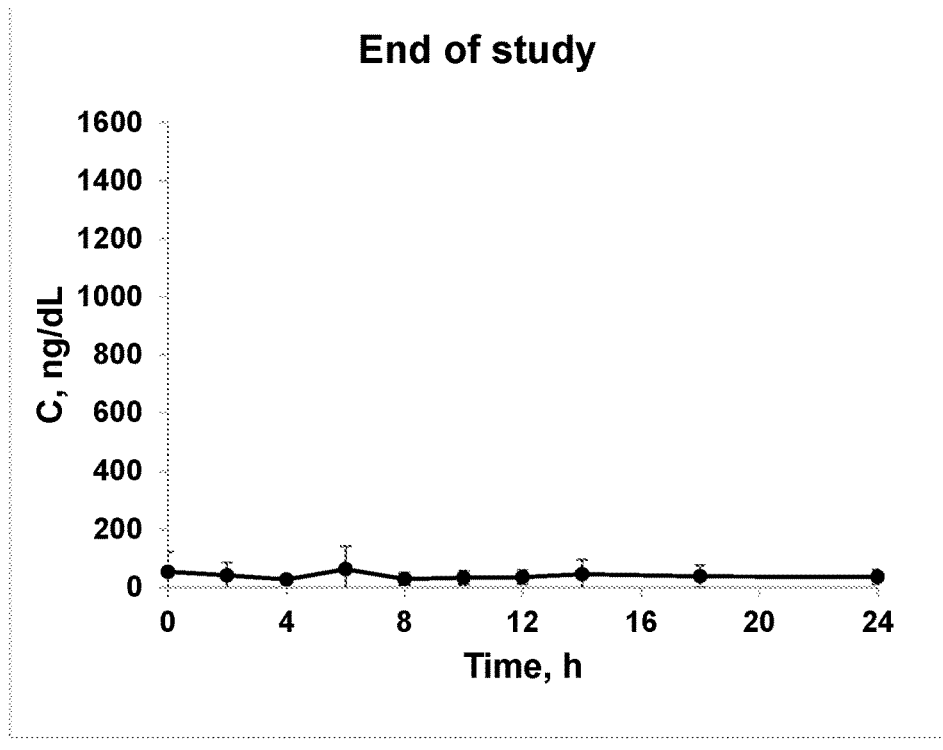
FIG. 23B shows the mean, baseline, EOS plasma T concentration over 24 hours in male dogs used in the multi-day dose escalation study described in Example 14.
Figure 23C:
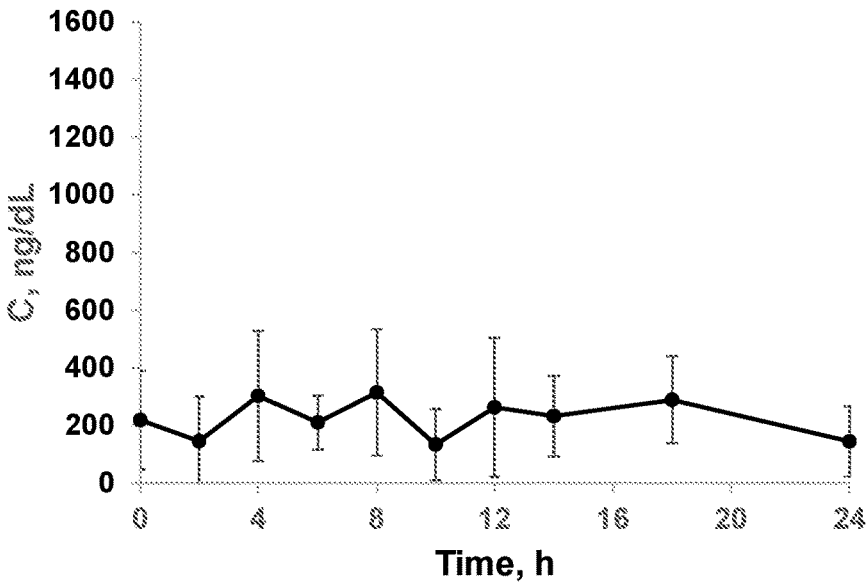
FIG. 23C shows the mean plasma T concentration over 24 hours at D1 of 30 mg/BID TSX-049 dosing in male dogs used in the multi-day dose escalation study described in Example 14.
Figure 23D:
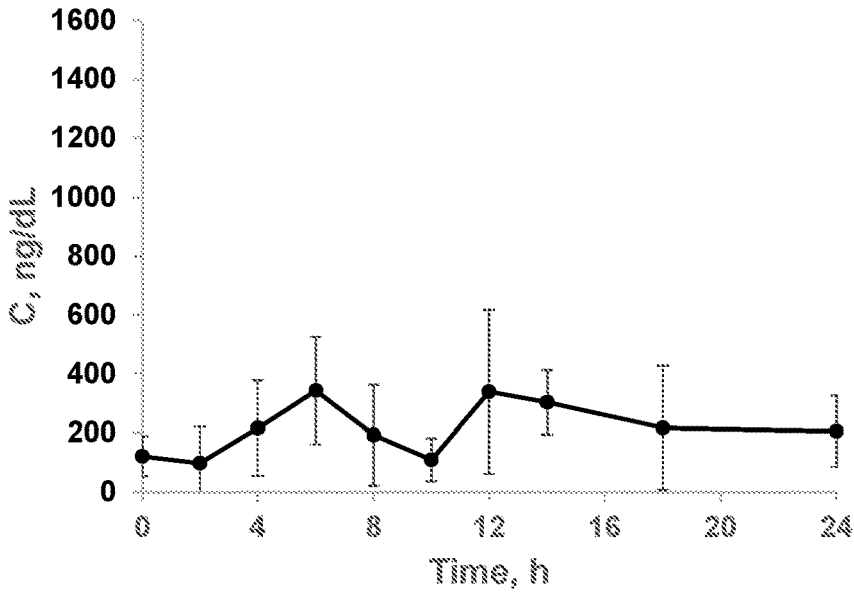
FIG. 23D shows the mean plasma T concentration over 24 hours at D5 of 30 mg/BID TSX-049 dosing in male dogs used in the multi-day dose escalation study described in Example 14.
Figure 23E:
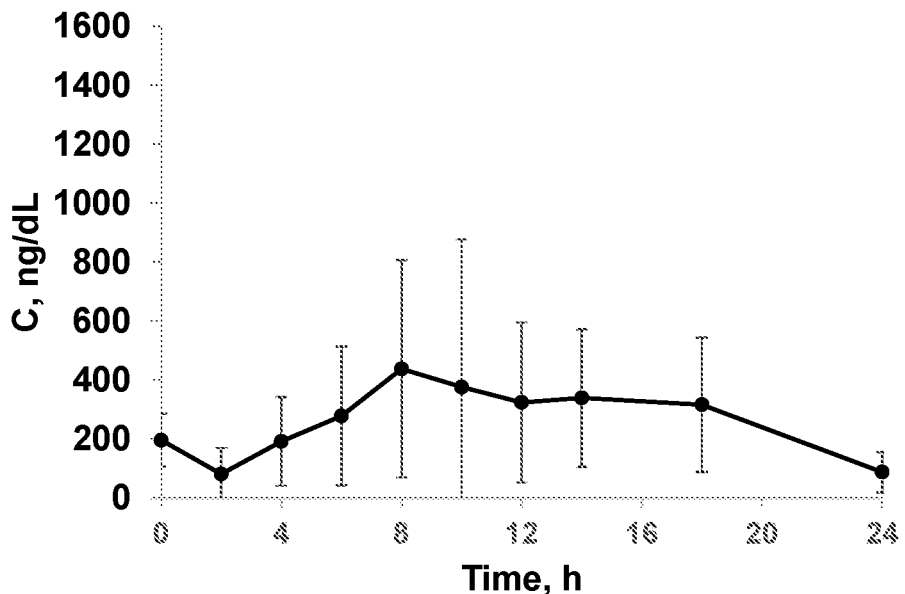
FIG. 23E shows the mean plasma T concentration over 24 hours at D1 of 60 mg/BID TSX-049 dosing in male dogs used in the multi-day dose escalation study described in Example 14.
Figure 23F:
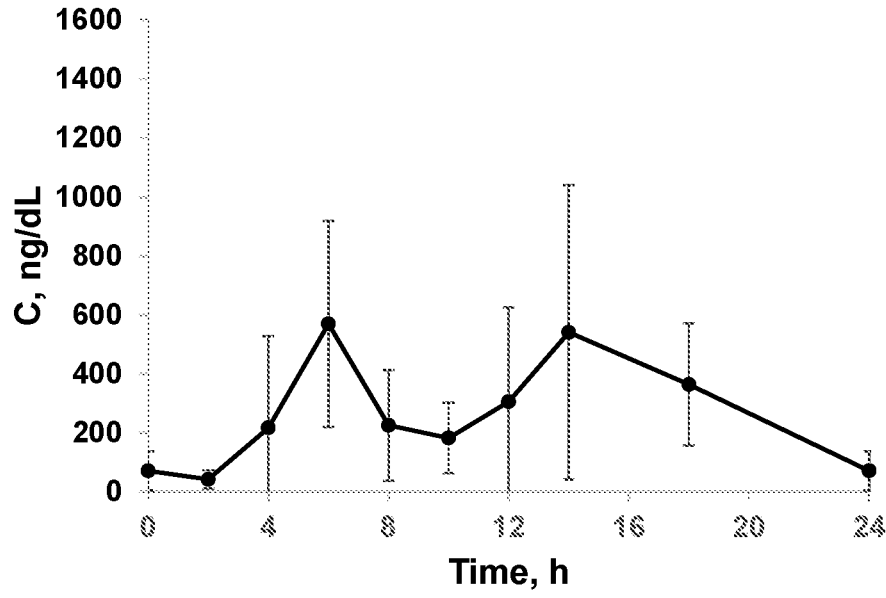
FIG. 23F shows the mean plasma T concentration over 24 hours at D5 of 60 mg/BID TSX-049 dosing in male dogs used in the multi-day dose escalation study described in Example 14.
Figure 23G:
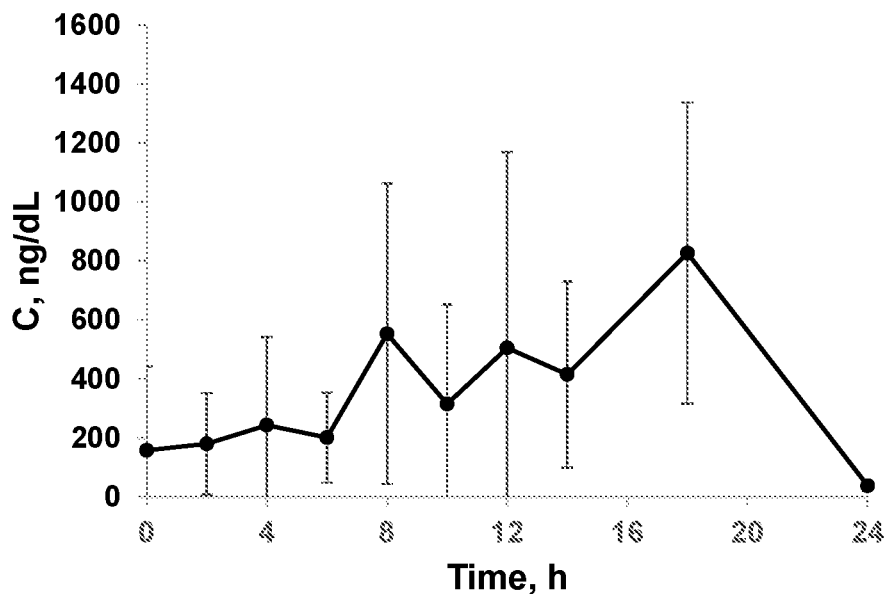
FIG. 23G shows the mean plasma T concentration over 24 hours at D1 of 120 mg/BID TSX-049 dosing in male dogs used in the multi-day dose escalation study described in Example 14.
Figure 23H:
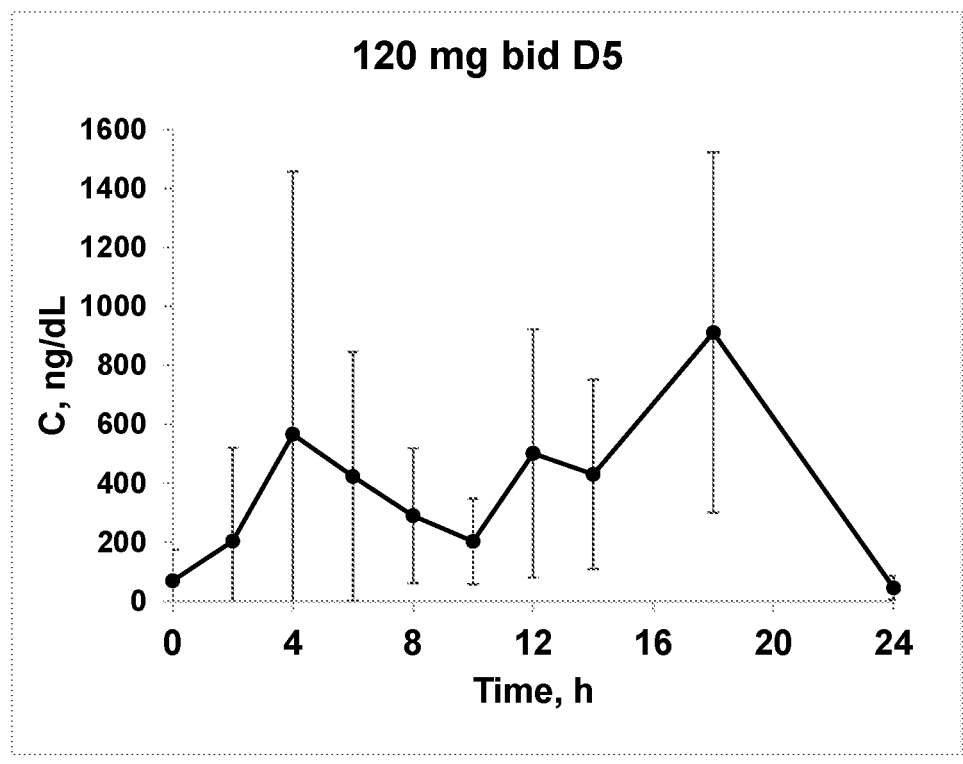
FIG. 23H shows the mean plasma T concentration over 24 hours at D5 of 120 mg/BID TSX-049 dosing in male dogs used in the multi-day dose escalation study described in Example 14.
Figure 24A:
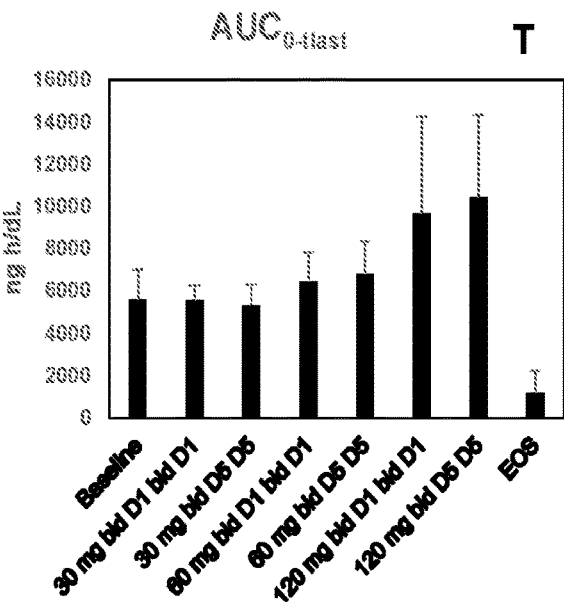
FIG. 24A shows the mean $AUC_{0-tlast}$ for T at each time point and TU dose in the multi-day dose escalation study described in Example 14.
Figure 24B:
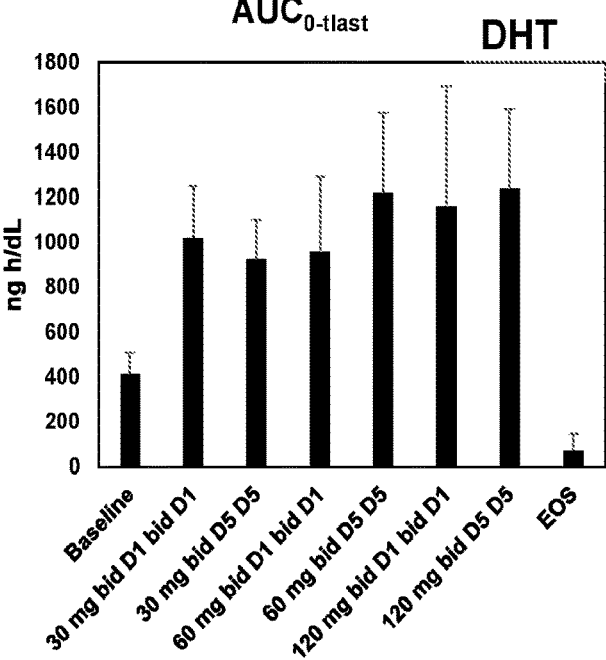
FIG. 24B shows the mean $AUC_{0-tlast}$ for DHT at each time point and TU dose in the multi-day dose escalation study described in Example 14.
Figure 24C:
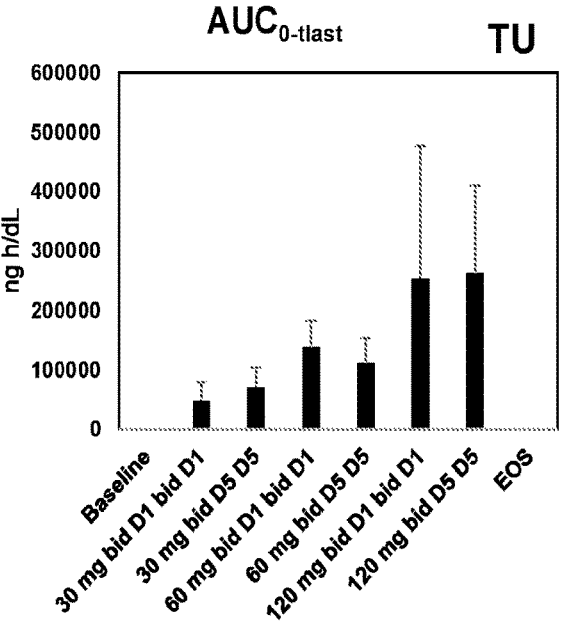
FIG. 24C shows the mean $AUC_{0-tlast}$ for TU at each time point and TU dose in the multi-day dose escalation study described in Example 14.
Figure 24D:
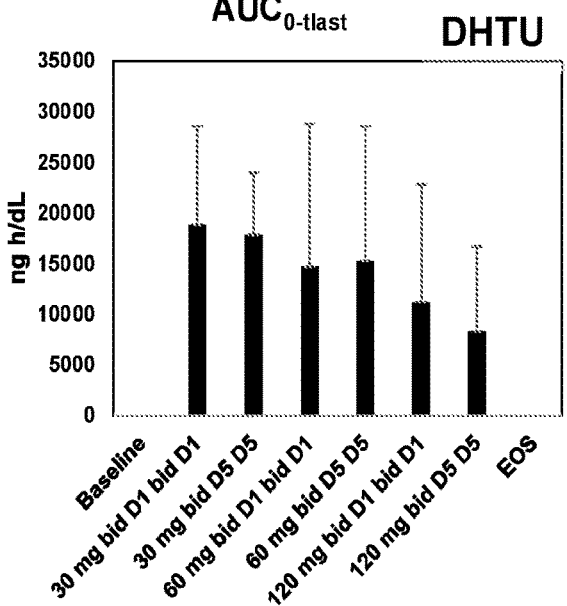
FIG. 24D shows the mean $AUC_{0-tlast}$ for DHTU at each time point and TU dose in the multi-day dose escalation study described in Example 14.
Figure 25A:
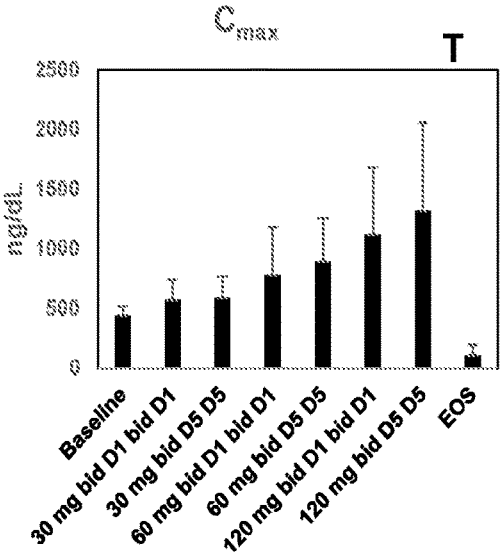
FIG. 25A shows the mean $C_{max}$ for T at each time point and TU dose in the multi-day dose escalation study described in Example 14.
Figure 25B:
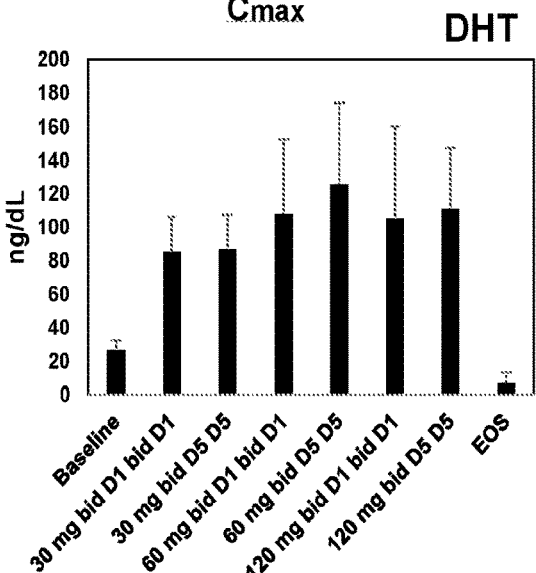
FIG. 25B shows the mean $C_{max}$ for DHT at each time point and TU dose in the multi-day dose escalation study described in Example 14.
Figure 25C:
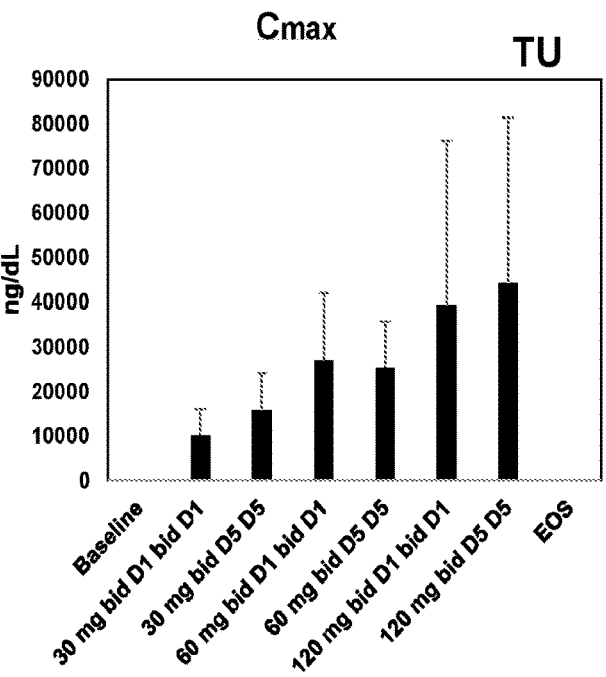
FIG. 25C shows the mean $C_{max}$ for TU at each time point and TU dose in the multi-day dose escalation study described in Example 14.
Figure 25D:
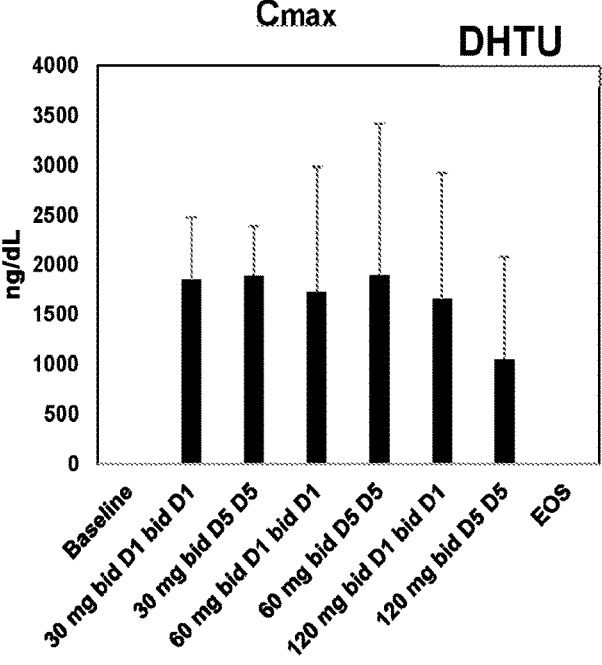
FIG. 25D shows the mean $C_{max}$ for DHTU at each time point and TU dose in the multi-day dose escalation study described in Example 14.
Figure 26A:
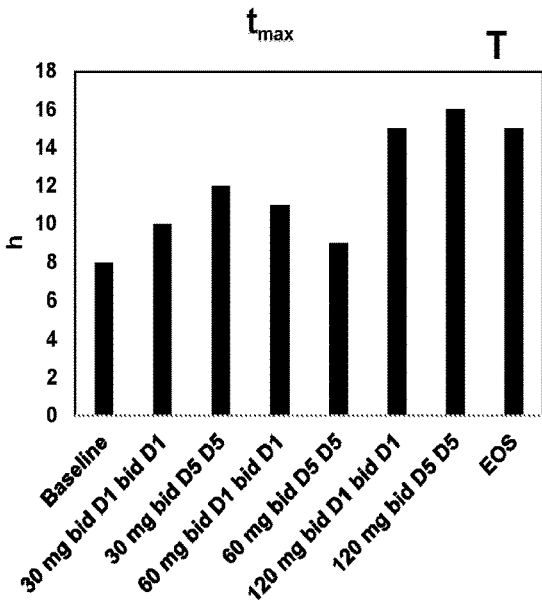
FIG. 26A shows the mean $t_{max}$ for T at each time point and TU dose in the multi-day dose escalation study described in Example 14.

Blood samples were taken from the dogs at: day 1 (predose baseline); day 8 (D1 of 30 mg dosing); day 12 (D5 of 30 mg BID dosing); day 18 (D1 of 60 mg BID dosing); day 22 (D5 of 60 mg BID dosing); day 27 (D1 of 120 mg BID dosing); day 32 (D5 of 120 mg BID dosing); and day 39-40 (end of study (EOS)). On the days prior to the blood draw timepoints, the dogs was were fasted overnight, and fed state dosing was performed the subsequent morning by serving the dogs food immediately after oral dosing, and then allowing dogs access to food for 2 hours. The second, oral dose was administered about 8 hours later, again followed by access to food immediately, then for an additional 2 hours. An exception to the foregoing protocol was that the dogs were not administered TSX-049 on day 1 of the study, when the predose plasma testosterone baseline levels were determined. Blood draws were performed by venipuncture of the jugular vein at 0, 2, 4, 6, 8, 12, 15, 18, 21 and 24 hours. Pharmacokinetic analysis of the blood plasma was performed to determine plasma levels, AUC, $C_{max}$, and $t_{max}$ parameters for testosterone (T), dihydrotestosterone (DHT), TU, and dihydrotestosterone undecanoate (DHTU). FIG. 23A shows the mean, baseline plasma T concentration over 24 hours on day 1 of the study. FIG. 23B shows the mean, baseline plasma T concentration over 24 hours at the end of the study (EOS) on day 39 or 40 of the study. The end of study baseline was lower than the predose baseline, which was expected, as it is consistent with a negative feedback effect on endogenous T levels. FIGS. 23C-H show the mean plasma T concentrations over 24 hours for the D1 and D5 timepoints for the 60 mg, 120 mg, and 240 mg daily TU doses. Table 14 summarizes the AUC parameter for T over the course of the study, and indicates, along with FIGS. 23C-23D, that the 30 mg/BID TU dose (60 mg daily) is not sufficient to enhance the endogenous 'T' levels. The plasma concentration data from the D1 and D5 timepoints of the 120 mg/BID (240 mg daily) phase of the study demonstrated that this dose was sufficient to overcome the endogenous 'T' levels. Indeed, $C_{max}$ increased with dose when the dose was over 60 mg (see FIG. 25A). The 120 mg dose showed a strong increase in exposure, especially noticeable later in the day. This is consistent with the prolongation of the median $t_{max}$ (see FIG. 26A), as well as with lymphatic absorption of TU. In addition, the AUC for DHT stayed relatively constant with TU dosing by TSX-049 (see FIG. 24B), which was a desirable finding. It was also observed that the AUC for TU increased in a near-dose proportional manner across all 3 doses (see FIG. 24C), an observation that was expected as TU would not be subject to the effects of negative feedback. The levels of the undecanoate forms in plasma were also significantly higher than those of the unconjugated components (FIGS. 24A-24D), though DHTU tended to decrease with increased TU dose, and with repeated administration of the same dose. See FIG. 24D.

TABLE 14

| | | | $AUC_{0-tlast}$ (ng h/dL) for T plasma levels | | | | | |
|---|---|---|---|---|---|---|---|---|
| | Baseline | 30 mg bid D 1 | 30 mg bid D 5 | 60 mg bid D 1 | 60 mg bid D 5 | 120 mg bid D 1* | 120 mg bid D5 | EOS |
| Mean | 5573 | 5542 | 5319 | 6446 | 5504 | 9657 | 10442 | 1191 |
| SD | 1413 | 724 | 966 | 1768 | 1768 | 4602 | 3906 | 1032 |
| Min | 3919 | 4125 | 3990 | 4446 | 2973 | 5104 | 6063 | 224 |
| Max | 7977 | 6298 | 6892 | 9480 | 8558 | 18392 | 18182 | 3780 |
| Median | 5186 | 5643 | 5023 | 6290 | 5205 | 7992 | 9445 | 825 |
| Geomean | 5422 | 5495 | 5242 | 6327 | 5241 | 8784 | 9827 | 906 |
| n | 10 | 10 | 10 | 10 | 10 | 10 | 10 | 10 |

*$AUC_{(0-18\,h)}$

TABLE 15

| | | | $C_{max}$ ng/dL | | | | | |
|---|---|---|---|---|---|---|---|---|
| | Baseline | 30 mg bid D 1 | 30 mg bid D 5 | 60 mg bid D 1 | 60 mg bid D 5 | 120 mg bid D 1 | 120 mg bid D 5 | EOS |
| Mean | 442.3 | 571.8 | 585.7 | 777.5 | 891.5 | 1120.3 | 1316.2 | 108.6 |
| SD | 77.4 | 166.8 | 179.2 | 400.5 | 367.0 | 559.1 | 741.9 | 90.0 |
| Min | 354.0 | 358.0 | 313.0 | 271.0 | 540.0 | 647.0 | 467.0 | 19.0 |
| Max | 599.0 | 820.0 | 891.0 | 1760.0 | 1730.0 | 2130.0 | 2930.0 | 273.0 |
| Median | 426.5 | 569.5 | 573.5 | 736.0 | 809.0 | 960.0 | 1125.0 | 79.0 |
| Geomean | 436.5 | 549.2 | 559.9 | 698.5 | 834.9 | 1016.0 | 1163.3 | 80.3 |
| n | 10 | 10 | 10 | 10 | 10 | 10 | 10 | 10 |

Figure 26B:
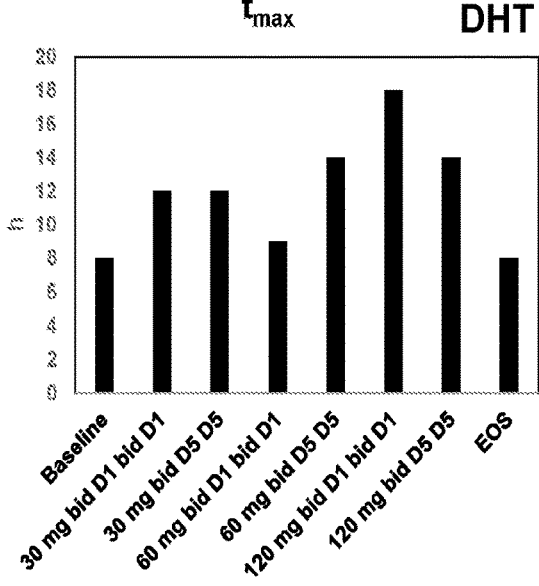
FIG. 26B shows the mean $t_{max}$ for DHT at each time point and TU dose in the multi-day dose escalation study described in Example 14.
Figure 26C:
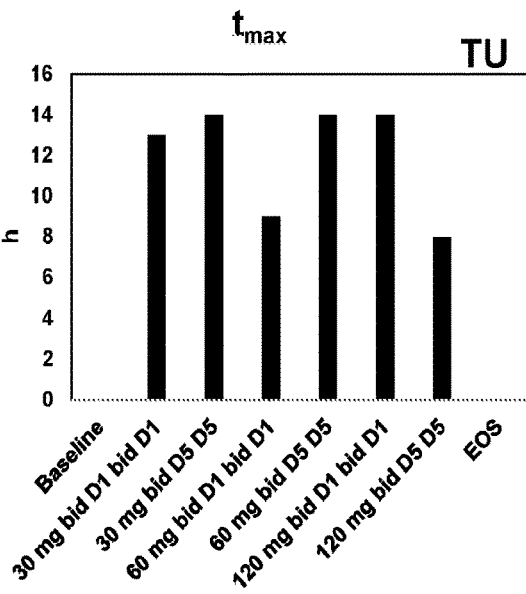
FIG. 26C shows the mean $t_{max}$ for TU at each time point and TU dose in the multi-day dose escalation study described in Example 14.
Figure 26D:
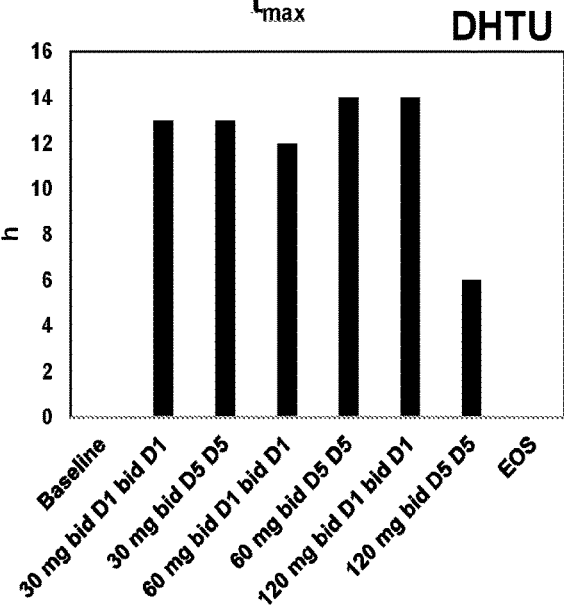
FIG. 26D shows the mean $t_{max}$ for DHTU at each time point and TU dose in the multi-day dose escalation study described in Example 14.

With respect to the $t_{max}$ parameter, there was similar trend observed between the $t_{max}$ values for T and DHT. See FIGS. 26A and 26B. Analogous similarities in $t_{max}$ trends were also observed for TU and DHTU. See FIGS. 26C and 26D.

TABLE 16

| | | | $t_{max}$ h | | | | | |
|---|---|---|---|---|---|---|---|---|
| | Baseline | 30 mg bid D 1 | 30 mg bid D 5 | 60 mg bid D 1 | 60 mg bid D 5 | 120 mg bid D 1 | 120 mg bid D 5 | EOS |
| Mean | 8 | 10 | 12 | 11 | 10 | 13 | 14 | 14 |
| SD | 4 | 6 | 5 | 5 | 5 | 7 | 5 | 10 |
| Min | 0 | 0 | 2 | 2 | 6 | 0 | 4 | 2 |
| Max | 18 | 18 | 18 | 18 | 18 | 18 | 18 | 24 |
| Median | 8 | 10 | 12 | 11 | 9 | 15 | 16 | 15 |
| Geomean | | | | | | | | |
| n | 10 | 10 | 10 | 10 | 10 | 10 | 10 | 10 |

What is claimed:

1. A proliposomal powder dispersion consisting of testosterone undecanoate (TU) and dipalmitoyl phosphatidyl-choline (DPPC), wherein the weight/weight (w/w) ratio of TU:DPPC in the proliposomal powder dispersion ranges from (0.9-1.1):(1.8-2.2).

2. An oral dosage form comprising a proliposomal powder dispersion of claim 1.

3. The oral dosage of claim 2, further comprising mannitol, wherein the w/w ratio of the proliposomal powder dispersion to mannitol ranges from (0.9-1.1) (1.13-1.37).

4. The oral dosage form of claim 1, wherein the oral dosage form comprises an enteric-coated capsule.

5. The oral dosage form of claim 4, wherein the enteric coated capsule material comprises plant-derived hydroxy-propyl methylcellulose (HPMC).

6. The oral dosage form of claim 4, wherein the enteric coating material comprises methacrylic acid copolymer.

7. A method of testosterone replacement therapy (TRT) for an individual in need thereof, comprising administering an oral dosage form of claim 2.

8. The method of TRT of claim 7, wherein the TRT treats a condition in the individual in need thereof that causes a low endogenous level of testosterone in the plasma of the individual.

9. The method of TRT of claim 8, wherein the low endogenous level of testosterone results from an injury, an infection, a loss of the testicles, chemotherapy, radiation treatment, genetic abnormalities, hemochromatosis, dysfunction of the pituitary gland, inflammatory disease, medication side effect, chronic kidney failure, liver cirrhosis, stress, alcoholism, obesity, Kallman's syndrome, male hypogonadism, or testosterone deficiency syndrome (TDS).

10. The method of TRT of claim 8, wherein the pre-therapy plasma level of testosterone is 300 ng/dL or less.

11. The proliposomal powder dispersion of claim 1, wherein the w/w ratio of TU:DPPC is about 1:2.

12. The oral dosage form of claim 2, wherein the w/w ratio of TU:DPPC in the proliposomal powder dispersion is about 1:2.

* * * * *